(12) United States Patent
Arai et al.

(10) Patent No.: US 9,590,187 B2
(45) Date of Patent: Mar. 7, 2017

(54) SUBSTITUENT-ELIMINABLE DIKETOPYRROLOPYRROLE DERIVATIVE, ORGANIC SEMICONDUCTOR MATERIAL PRECURSOR SOLUTION, ORGANIC SEMICONDUCTOR MATERIAL, AND ORGANIC SEMICONDUCTOR MATERIAL FILM

(71) Applicants: Ryota Arai, Shizuoka (JP); Yoshiki Yanagawa, Shizuoka (JP)

(72) Inventors: Ryota Arai, Shizuoka (JP); Yoshiki Yanagawa, Shizuoka (JP)

(73) Assignee: RICOH COMPANY, LTD., Tokyo (JP)

( * ) Notice: Subject to any disclaimer, the term of this patent is extended or adjusted under 35 U.S.C. 154(b) by 287 days.

(21) Appl. No.: 14/334,785

(22) Filed: Jul. 18, 2014

(65) Prior Publication Data

US 2015/0041724 A1 Feb. 12, 2015

(30) Foreign Application Priority Data

Aug. 7, 2013 (JP) .................................. 2013-164022

(51) Int. Cl.
*H01B 1/12* (2006.01)
*H01L 51/00* (2006.01)
(Continued)

(52) U.S. Cl.
CPC ........ *H01L 51/0068* (2013.01); *C07D 487/04* (2013.01); *C08G 61/126* (2013.01); *H01L 51/0053* (2013.01); *C08G 2261/135* (2013.01); *C08G 2261/1412* (2013.01); *C08G 2261/1644* (2013.01); *C08G 2261/3223* (2013.01); *C08G 2261/334* (2013.01); *C08G 2261/344* (2013.01); *C08G 2261/364* (2013.01);
(Continued)

(58) Field of Classification Search
CPC ......................................................... H01B 1/12
See application file for complete search history.

(56) References Cited

U.S. PATENT DOCUMENTS

2010/0326525 A1   12/2010   Nguyen et al.

FOREIGN PATENT DOCUMENTS

JP   2011-501743   1/2011
WO   WO2009/047104 A2   4/2009

*Primary Examiner* — William Young
(74) *Attorney, Agent, or Firm* — Cooper & Dunham LLP

(57) ABSTRACT

A substituent-eliminable diketopyrrolopyrrole derivative represented by the following formula (I) is provided.

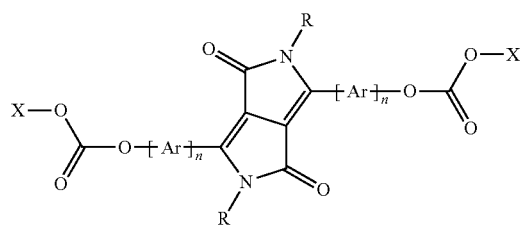

(I)

In the formula (I), R represents a substituted or unsubstituted alkyl group; X represents a substituted or unsubstituted alkyl group; Ar represents a substituted or unsubstituted aromatic group or a substituted or unsubstituted heteroaromatic group; and n represents an integer of from 1 to 4.

3 Claims, 6 Drawing Sheets

(51) Int. Cl.
*C07D 487/04* (2006.01)
*C08G 61/12* (2006.01)
(52) U.S. Cl.
CPC .. *C08G 2261/411* (2013.01); *C08G 2261/592* (2013.01); *C08G 2261/64* (2013.01); *C08G 2261/76* (2013.01); *C08G 2261/80* (2013.01); *C08G 2261/91* (2013.01); *C08G 2261/92* (2013.01); *C08G 2261/94* (2013.01); *C08G 2261/95* (2013.01); *H01B 1/12* (2013.01)

SUBSTITUENT-ELIMINABLE DIKETOPYRROLOPYRROLE DERIVATIVE, ORGANIC SEMICONDUCTOR MATERIAL PRECURSOR SOLUTION, ORGANIC SEMICONDUCTOR MATERIAL, AND ORGANIC SEMICONDUCTOR MATERIAL FILM

CROSS-REFERENCE TO RELATED APPLICATIONS

This patent application is based on and claims priority pursuant to 35 U.S.C. §119(a) to Japanese Patent Application No. 2013-164022, filed on Aug. 7, 2014, in the Japan Patent Office, the entire disclosure of which is hereby incorporated by reference herein.

BACKGROUND

Technical Field

The present invention relates to a substituent-eliminable diketopyrrolopyrrole derivative, an organic semiconductor material precursor solution, an organic semiconductor material, and an organic semiconductor material film.

Description of the Related Art

Recently, there has been an increase in research and development for sensors using organic semiconductor materials, organic light-emitting diodes, organic field-effect transistors, and organic semiconductors for solar cells.

Materials soluble in organic solvents are known as organic semiconductor materials. Such materials are easily processible into thin films by simple wet processes, such as printing process and spin coat process, even on plastic substrates that will have low heat resistance. The utility of plastic substrates in combination with such materials soluble in organic solvents leads to reduction in weight and cost for resulting electronic devices such as displays. Various other applications are expected owing to such a flexibility of plastic substrates.

Japanese Patent Application Publication No. 2011-501743 discloses a derivative of low-molecular-weight diketopyrrolopyrrole as a p-type semiconductor material for use in solar cells. The derivative has a thiophene ring to which a long straight-chain or branched-chain alkyl group is directly introduced to the third or fourth position thereof.

U.S. Patent Application Publication No. 2010/0326525 also discloses a derivative of low-molecular-weight diketopyrrolopyrrole. The derivative has a thiophene ring to which an alkyl group is directly introduced to the fifth position thereof. Both of the references have attempted to introduce long-chain alkyl group to diketopyrrolopyrrole derivative to improve its solubility in organic solvents and compatibility with n-type semiconductor materials for use in solar cells, which may improve incident photoelectric conversion efficiency of solar cells.

SUMMARY

In accordance with some embodiments, a substituent-eliminable diketopyrrolopyrrole derivative represented by the following formula (I) is provided.

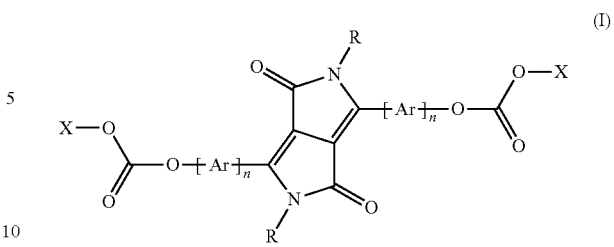

(I)

In the formula (I), R represents a substituted or unsubstituted alkyl group; X represents a substituted or unsubstituted alkyl group; Ar represents a substituted or unsubstituted aromatic group or a substituted or unsubstituted heteroaromatic group; and n represents an integer of from 1 to 4.

In accordance with some embodiments, an organic semiconductor material precursor solution is provided. The organic semiconductor material precursor solution includes the above substituent-eliminable diketopyrrolopyrrole derivative represented by the formula (I) and a solvent.

In accordance with some embodiments, an organic semiconductor material is provided. The organic semiconductor material includes a diketopyrrolopyrrole compound represented by the following formula (II).

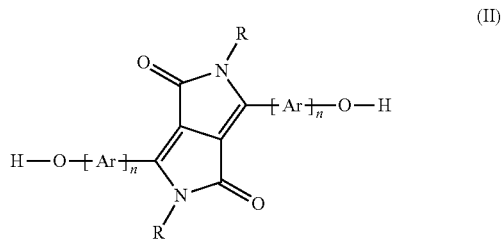

(II)

In the formula (II), R represents a substituted or unsubstituted alkyl group; Ar represents a substituted or unsubstituted aromatic group or a substituted or unsubstituted heteroaromatic group; and n represents an integer of from 1 to 4. The diketopyrrolopyrrole compound represented by the formula (II) is obtained by converting the above substituent-eliminable diketopyrrolopyrrole derivative represented by the formula (I) by giving energy thereto.

In accordance with some embodiments, an organic semiconductor material film is provided. The organic semiconductor material film includes the above diketopyrrolopyrrole compound represented by the following formula (II) obtained by converting the above substituent-eliminable diketopyrrolopyrrole derivative represented by the formula (I) by giving energy thereto.

BRIEF DESCRIPTION OF THE SEVERAL VIEWS OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION

Figure 1:
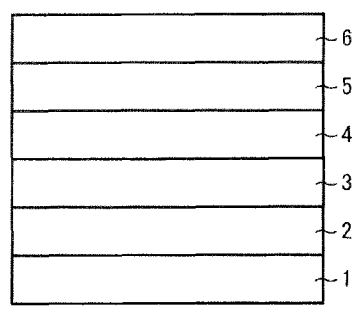
FIG. 1 is a schematic view illustrating a configuration example of an organic solar cell.

Embodiments of the present invention are described in detail below with reference to accompanying drawings. In describing embodiments illustrated in the drawings, specific terminology is employed for the sake of clarity. However, the disclosure of this patent specification is not intended to be limited to the specific terminology so selected, and it is to be understood that each specific element includes all technical equivalents that operate in a similar manner and achieve a similar result.

For the sake of simplicity, the same reference number will be given to identical constituent elements such as parts and materials having the same functions and redundant descriptions thereof omitted unless otherwise stated.

Japanese Patent Application No. 2013-052513 discloses a diketopyrrolopyrrole derivative to which an eliminable substituent is introduced to nitrogen atom. When the derivative is formed into a film while eliminating the substituent, its absorption spectrum shifts toward shorter wavelength, which is a disadvantageous feature when considering application to organic-thin-film solar cells.

One object of the present disclosure is to provide a diketopyrrolopyrrole derivative which has a high solubility before being heated and the solubility of which is extremely lowered upon production of hydroxyl group by application of heat; and does not shift its absorption spectrum toward shorter wavelengths upon elimination of its substituent.

It is clear from the following detailed and specific descriptions that, according to an embodiment of the present invention, a substituent-eliminable diketopyrrolopyrrole derivative is provided which has high solubility in organic solvents and is easily synthesizable. Further, an organic semiconductor material is provided which has no unstable terminal substituent (i.e., an olefin group such as vinyl group and propenyl group) and is obtainable through a substituent elimination reaction of the substituent-eliminable diketopyrrolopyrrole derivative.

According to an embodiment, it is possible that the substituent elimination reaction of the substituent-eliminable diketopyrrolopyrrole derivative proceeds at lower energy compared to that of related-art substituent-eliminable compounds. According to an embodiment, an organic semiconductor film consisting of an organic semiconductor material is obtainable by applying a solution including the substituent-eliminable diketopyrrolopyrrole derivative (as an organic semiconductor precursor) and a solvent to form an organic film and then exposing the film to the elimination reaction.

The absorption characteristic does not shift toward shorter wavelengths even after the substituent has been eliminated. With use of such an organic semiconductor film, organic electronic devices can be advantageously provided.

Embodiments of the present invention are described in detail below with reference to accompanying drawings. In describing embodiments illustrated in the drawings, specific terminology is employed for the sake of clarity. However, the disclosure of this patent specification is not intended to be limited to the specific terminology so selected, and it is to be understood that each specific element includes all technical equivalents that operate in a similar manner and achieve a similar result.

1. Substituent-Eliminable Diketopyrrolopyrrole Derivative and Diketopyrrolopyrrole Compound Obtainable by Elimination Reaction The substituent-eliminable diketopyrrolopyrrole derivative (may be hereinafter referred to as "organic semiconductor material precursor" or "substituent-eliminable derivative") according to an embodiment of the present invention is represented by the following formula (I):

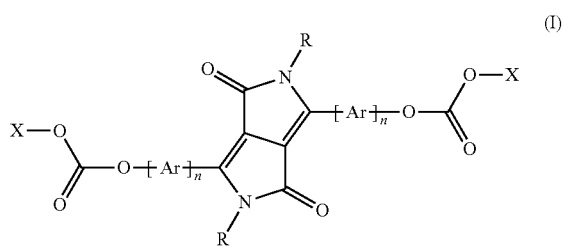

wherein R represents a substituted or unsubstituted alkyl group; X represents a substituted or unsubstituted alkyl group; Ar represents a substituted or unsubstituted aromatic group or a substituted or unsubstituted heteroaromatic group; and n represents an integer of from 1 to 4.

The organic semiconductor material precursor has a specific solvent-soluble substituent. By giving energy (external stimuli) to it, the solvent-soluble substituent will be eliminated and an objective diketopyrrolopyrrole compound will be obtained.

In the formula (I), the specific solvent-soluble substituent is represented by the following formula (IA):

wherein X represents a substituted or unsubstituted alkyl group.

By giving energy (external stimuli) to it, the solvent-soluble substituent will be eliminated and the substituent-eliminable derivative represented by the formula (I) is converted into a compound represented by the following formula (II):

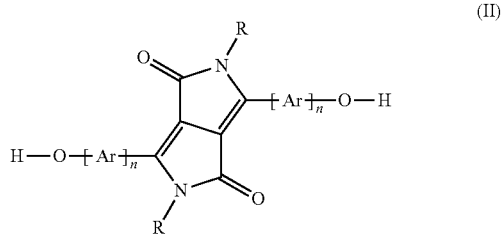

wherein R represents a substituted or unsubstituted alkyl group; Ar represents a substituted or unsubstituted aromatic group or a substituted or unsubstituted heteroaromatic group; and is represents an integer of from 1 to 4.

The alkyl group in the formulae (I) and (II) has a carbon number of from 1 to 30. The alkyl group may be either straight-chain or branched-chain. The alkyl group may also be a cycloalkyl group.

Specific examples of such alkyl groups include, but are not limited to, methyl group, ethyl group, n-propyl group, i-propyl group, n-butyl group, i-butyl group, tert-butyl group, sec-butyl group, 3-methylbutyl group, n-pentyl group, n-hexyl group, 2-ethylhexyl group, n-heptyl group, n-octyl group, n-nonyl group, n-decyl group, n-dodecyl group, and n-lauryl group. Each of these alkyl groups may have a substituent.

Specific examples of possible substituents include, but are not limited to, hydroxy group; alkyl groups having a carbon number of 1 to 12 such as methyl group, ethyl group, tert-butyl group, and octyl group; alkoxy groups having a carbon number of 1 to 12 such as methoxy group and ethoxy group; aryl groups having a carbon number of 6 to 12 such as phenyl group and naphthyl group; aralkyl groups having a carbon number of 7 to 12 such as benzyl group; acyl groups having a carbon number of 2 to 4 such as glycidyloxy group and acetyl group; acyloxy groups having a carbon number of 1 to 12 such as acetyloxy group; amino groups; amino groups substituted with one or two alkyl group(s) having a carbon number of 1 to 12 such as methylamino group, ethylamino group, and dimethylamino group; halogeno groups (halogen atoms) such as fluoro group (fluorine atom), chloro group (chlorine atom), and bromo group (bromine atom); oxo group (=O); carboxy group (—COOH); and alkoxy groups and alkylthio groups obtainable by introducing oxygen or sulfur atom to the binding sites of the above-described alkyl groups. Although a branched chain can be introduced, a straight chain is more preferable to avoid adverse effect on packing property of crystal.

The aromatic group in the formulae (I) and (II) is preferably selected from phenyl group, naphthyl group, and anthryl group. More preferably, the aromatic group is phenyl group. The aromatic group may have a substituent.

Specific examples of possible substituents include, but are not limited to, hydroxy group; alkyl groups having a carbon number of Ito 12 such as methyl group, ethyl group, tert-butyl group, and octyl group; alkoxy groups having a carbon number of 1 to 12 such as methoxy group and ethoxy group; aryl groups having a carbon number of 6 to 12 such as phenyl group and naphthyl group; aralkyl groups having a carbon number of 7 to 12 such as benzyl group; acyl groups having a carbon number of 2 to 4 such as glycidyloxy group and acetyl group; acyloxy groups having a carbon number of 1 to 12 such as acetyloxy group; amino groups; amino groups substituted with one or two alkyl group(s) having a carbon number of Ito 12 such as methylamino group, ethylamino group, and dimethylamino group; halogeno groups (halogen atoms) such as fluoro group (fluorine atom), chloro group (chlorine atom), and bromo group (bromine atom); oxo group (=O); carboxy group (—COOH); and alkoxy groups and alkylthio groups obtainable by introducing oxygen or sulfur atom to the binding sites of the above-described alkyl groups.

Specific examples of the heteroaromatic group include, but are not limited to, 5- or 6-position-substituted or unsubstituted aromatic heterocyclic compounds such as 2-furyl, 2-thienyl, 3-thienyl, 2-thienothienyl, 2-benzothienyl, and 2-pyrimidyl. In the formulae (I) and (II), n represents an integer of from 1 to 4, and is preferably 2 or 3.

The substituent-eliminable diketopyrrolopyrrole derivative has a specific eliminable solvent-soluble substituent, as described above, and has a feature that its absorption spectrum does not shift toward shorter wavelengths even after the substituent has been eliminated.

In this specification, "solvent-soluble" is defined as a state in which a solute has a solubility of 0.05% by weight or more in a solvent which has been heated to reflux and then cooled to room temperature. According to an embodiment, the substituent-eliminable diketopyrrolopyrrole derivative represented by the formula (I) preferably has a solubility of 0.1% by weight or more, more preferably 0.5% by weight or more, and most preferably 1.0% by weight or more.

In this specification, "insolubilization" is defined as an operation to decrease solubility of a solvent-soluble solute by one or more in the digit number. Specifically, before and after the elimination reaction, the solubility in a solvent which has been heated to reflux and then cooled to room temperature is decreased preferably from 0.05% by weight or more to 0.005% by weight or less, more preferably from 0.1% by weight or more to 0.01% by weight or less, much more preferably from 0.5% by weight or more to 0.05% by weight or less, and most preferably from 1.0% by weight or more to 0.1% by weight or less.

In this specification, "solvent-insoluble" is defined as a state in which a solute has a solubility of less than 0.01% by weight in a solvent which has been heated to reflux and then cooled to room temperature. According to an embodiment, the diketopyrrolopyrrole compound represented by the formula (II) preferably has a solubility of 0.005% by weight or less, and more preferably 0.001% by weight or less.

Usable solvents are not limited in determining the degree of solvent solubility and insolubility. For example, solubility may be determined in THF, toluene, chloroform, or methanol at, for example, 25° C.

In this specification, "absorption spectrum shifts toward shorter wavelengths" means that the absorption spectrum of a solute shifts toward a higher energy side than that in the solvent-soluble state. Specifically, in this situation, y<x is satisfied where the solute has maximum absorption wavelengths of x nm and y nm at the solvent-soluble and solvent-insoluble states, respectively.

Change in solubility is notably large before and after the elimination reaction, in other words, before and after the conversion from the substituent-eliminable diketopyrrolopyrrole derivative represented by the formula (I) to the diketopyrrolopyrrole compound represented by the formula (II). Thus, in a case in which a thin film layer is to be formed on the diketopyrrolopyrrole compound (hereinafter referred to as "specific diketopyrrolopyrrole compound" or "specific compound"), from which the eliminable substituent has been eliminated, the diketopyrrolopyrrole compound can be prevented from being affected by the solvent included in the solution for forming the thin film layer. This feature is advantageous in manufacturing organic electronic devices such as organic thin-film transistors, organic ELs, and organic solar cells.

Because the absorption characteristic does not shift toward shorter wavelengths by the conversion, the substituent-eliminable diketopyrrolopyrrole derivative is advantageous over materials whose absorption characteristic do shift toward shorter wavelengths in terms of energy, making it useful for organic electronic devices applying absorption such as organic solar cells.

Specific examples of the substituent-eliminable diketopyrrolopyrrole derivative according to an embodiment of the present invention are listed below, but are not limited thereto.

TABLE 1-1
Examples of Substituent-eliminable Diketopyrrolopyrrole Derivative (Part 1)
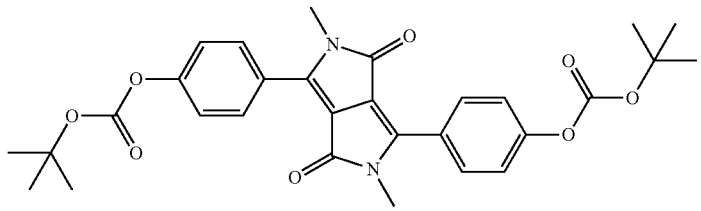 [SMILES: CN1C(=O)C2=C(c3ccc(OC(=O)OC(C)(C)C)cc3)N(C)C(=O)C2=C1c1ccc(OC(=O)OC(C)(C)C)cc1]
Substituent-eliminable Derivative No. 1
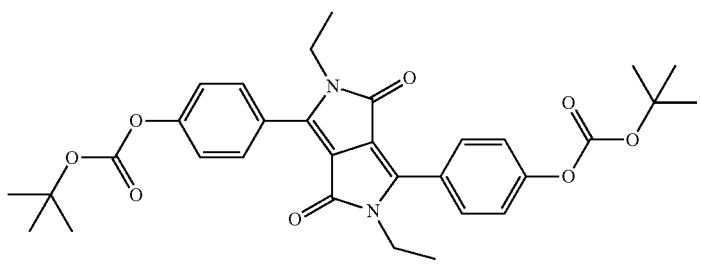 [SMILES: CCN1C(=O)C2=C(c3ccc(OC(=O)OC(C)(C)C)cc3)N(CC)C(=O)C2=C1c1ccc(OC(=O)OC(C)(C)C)cc1]
Substituent-eliminable Derivative No. 2
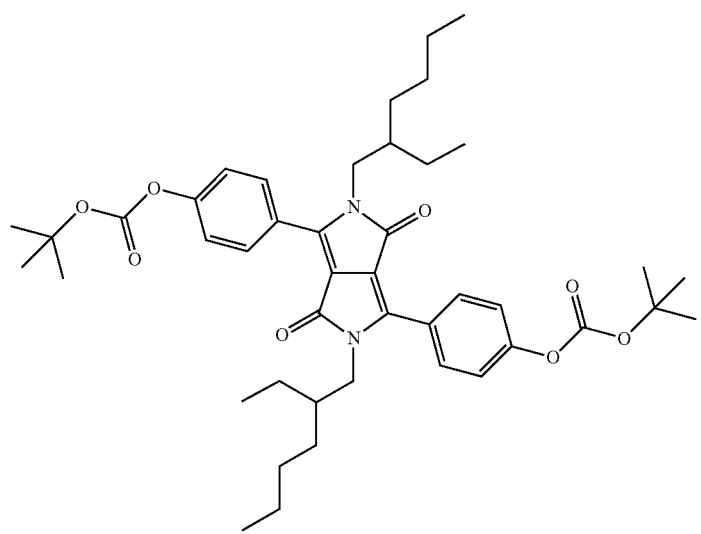 [SMILES: CCCCC(CC)CN1C(=O)C2=C(c3ccc(OC(=O)OC(C)(C)C)cc3)N(CC(CC)CCCC)C(=O)C2=C1c1ccc(OC(=O)OC(C)(C)C)cc1]
Substituent-eliminable Derivative No. 3
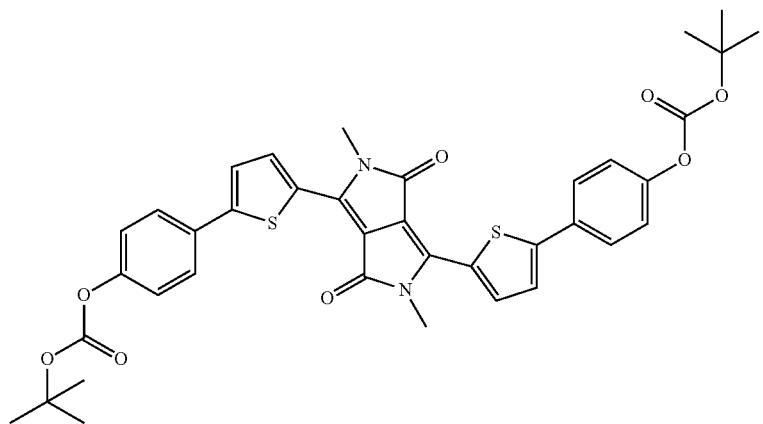 [SMILES: CN1C(=O)C2=C(c3ccc(-c4ccc(OC(=O)OC(C)(C)C)cc4)s3)N(C)C(=O)C2=C1c1ccc(-c2ccc(OC(=O)OC(C)(C)C)cc2)s1]
Substituent-eliminable Derivative No. 4

TABLE 1-2
Examples of Substituent-eliminable Diketopyrrolopyrrole Derivative (Part 2)
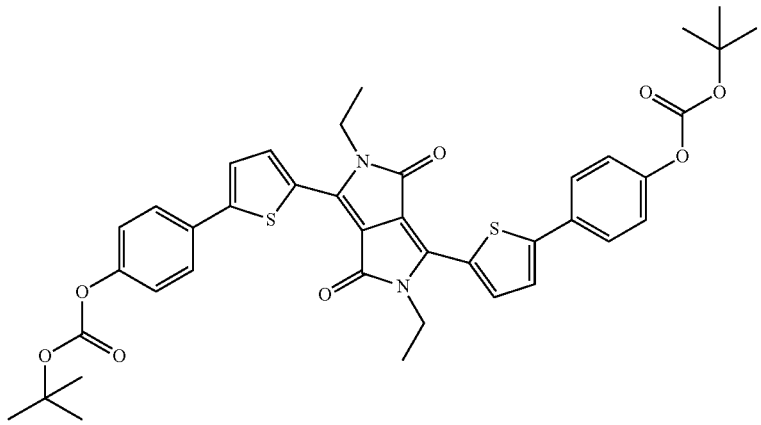 [SMILES: CCN1C(=O)C2=C(c3ccc(-c4ccc(OC(=O)OC(C)(C)C)cc4)s3)N(CC)C(=O)C2=C1c1ccc(-c2ccc(OC(=O)OC(C)(C)C)cc2)s1]
Substituent-eliminable Derivative No. 5
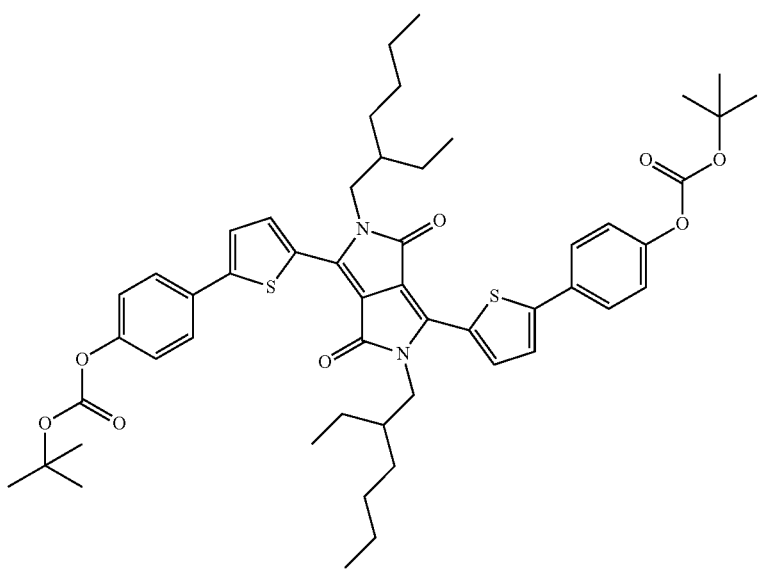 [SMILES: CCCCC(CC)CN1C(=O)C2=C(c3ccc(-c4ccc(OC(=O)OC(C)(C)C)cc4)s3)N(CC(CC)CCCC)C(=O)C2=C1c1ccc(-c2ccc(OC(=O)OC(C)(C)C)cc2)s1]
Substituent-eliminable Derivative No. 6
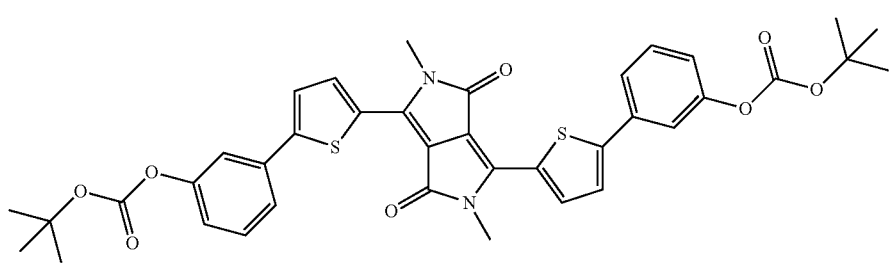 [SMILES: CN1C(=O)C2=C(c3ccc(-c4cccc(OC(=O)OC(C)(C)C)c4)s3)N(C)C(=O)C2=C1c1ccc(-c2cccc(OC(=O)OC(C)(C)C)c2)s1]
Substituent-eliminable Derivative No. 7
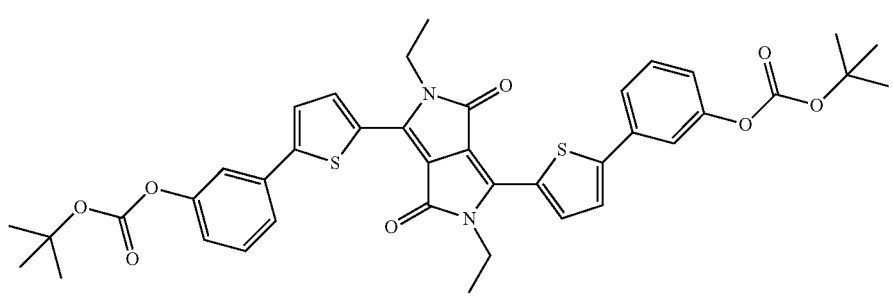 [SMILES: CCN1C(=O)C2=C(c3ccc(-c4cccc(OC(=O)OC(C)(C)C)c4)s3)N(CC)C(=O)C2=C1c1ccc(-c2cccc(OC(=O)OC(C)(C)C)c2)s1]
Substituent-eliminable Derivative No. 8

TABLE 1-3
Examples of Substituent-eliminable Diketopyrrolopyrrole Derivative (Part 3)
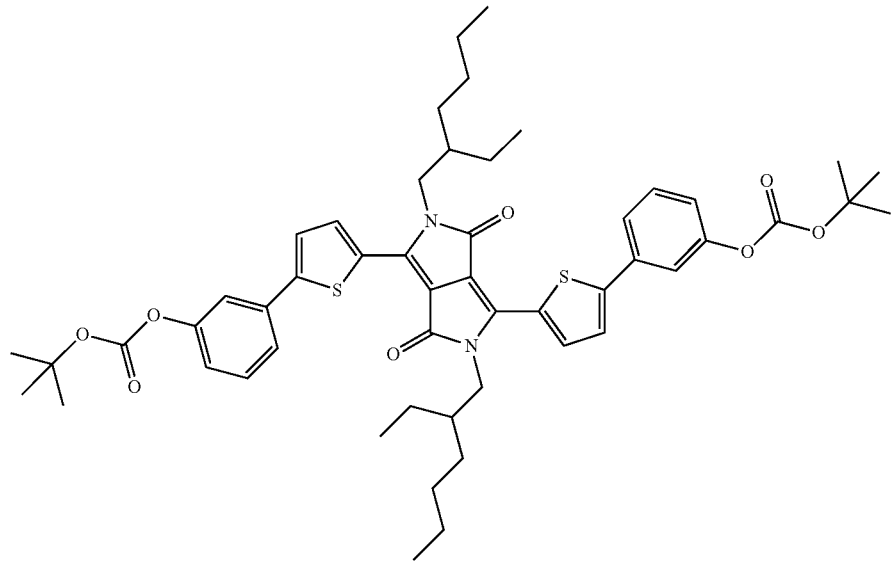 [SMILES: CCCCC(CC)CN1C(=O)C2=C(c3ccc(-c4cccc(OC(=O)OC(C)(C)C)c4)s3)N(CC(CC)CCCC)C(=O)C2=C1c1ccc(-c2cccc(OC(=O)OC(C)(C)C)c2)s1]
Substituent-eliminable Derivative No. 9
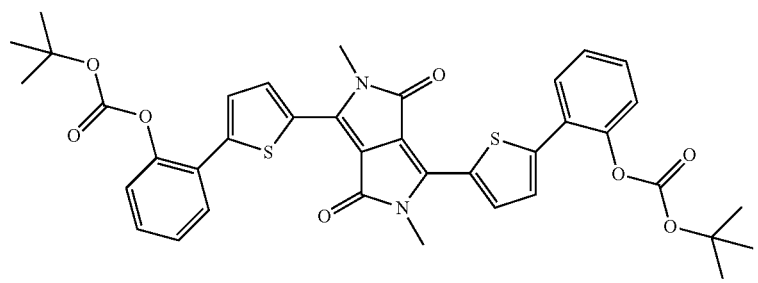 [SMILES: CN1C(=O)C2=C(c3ccc(-c4ccccc4OC(=O)OC(C)(C)C)s3)N(C)C(=O)C2=C1c1ccc(-c2ccccc2OC(=O)OC(C)(C)C)s1]
Substituent-eliminable Derivative No. 10
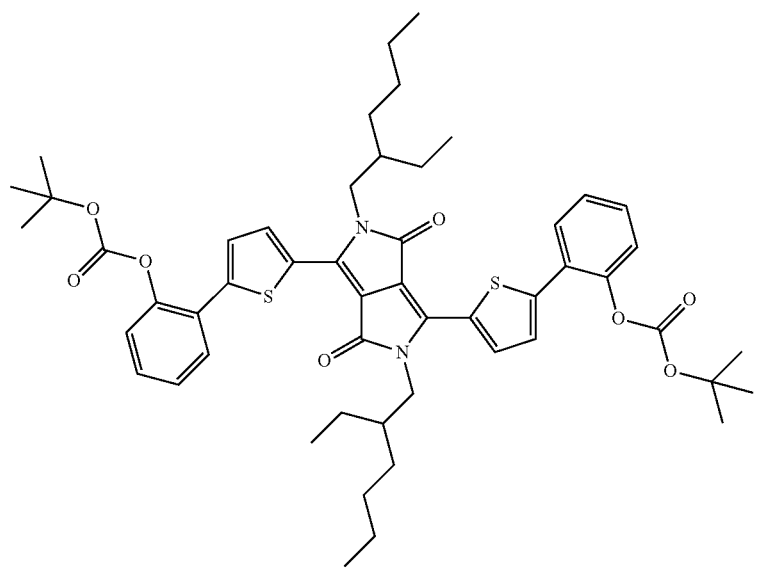 [SMILES: CCCCC(CC)CN1C(=O)C2=C(c3ccc(-c4ccccc4OC(=O)OC(C)(C)C)s3)N(CC(CC)CCCC)C(=O)C2=C1c1ccc(-c2ccccc2OC(=O)OC(C)(C)C)s1]
Substituent-eliminable Derivative No. 11

TABLE 1-4
Examples of Substituent-eliminable Diketopyrrolopyrrole Derivative (Part 4)
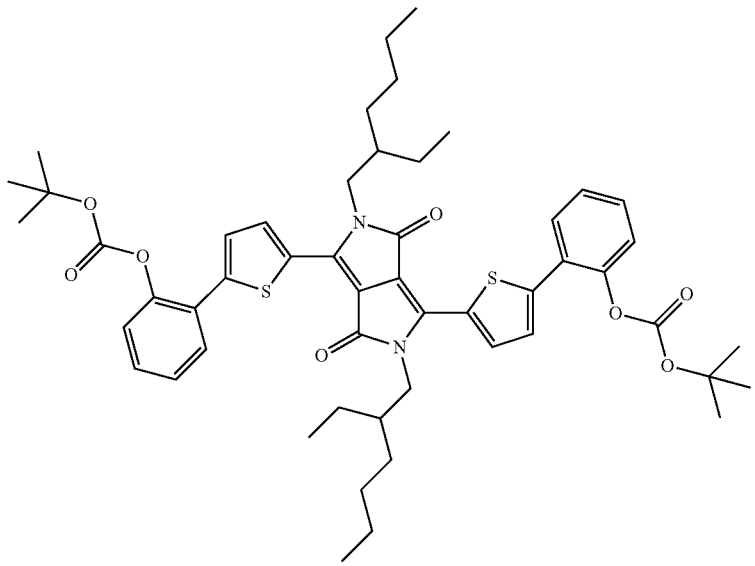 [SMILES: CCCCC(CC)CN1C(=O)C2=C(c3ccc(-c4ccccc4OC(=O)OC(C)(C)C)s3)N(CC(CC)CCCC)C(=O)C2=C1c1ccc(-c2ccccc2OC(=O)OC(C)(C)C)s1]
Substituent-eliminable Derivative No. 12
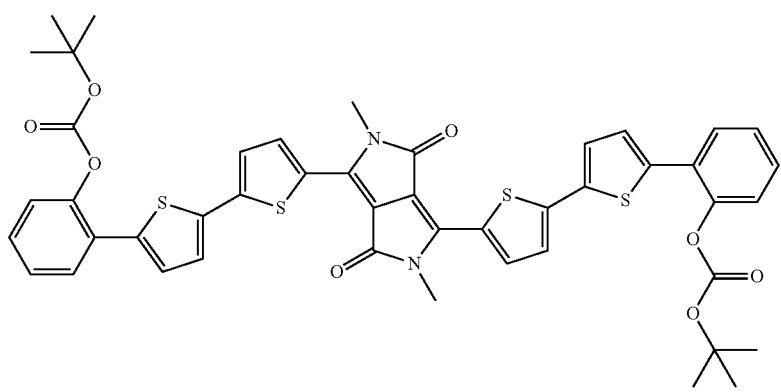 [SMILES: CN1C(=O)C2=C(c3ccc(-c4ccc(-c5ccccc5OC(=O)OC(C)(C)C)s4)s3)N(C)C(=O)C2=C1c1ccc(-c2ccc(-c3ccccc3OC(=O)OC(C)(C)C)s2)s1]
Substituent-eliminable Derivative No. 13
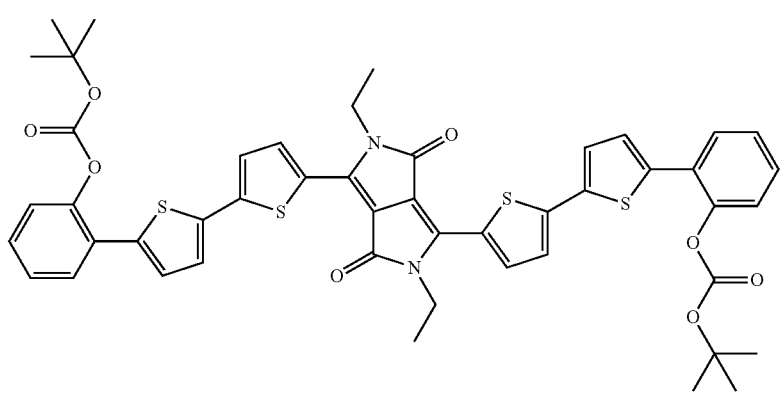 [SMILES: CCN1C(=O)C2=C(c3ccc(-c4ccc(-c5ccccc5OC(=O)OC(C)(C)C)s4)s3)N(CC)C(=O)C2=C1c1ccc(-c2ccc(-c3ccccc3OC(=O)OC(C)(C)C)s2)s1]
Substituent-eliminable Derivative No. 14

TABLE 1-5
Examples of Substituent-eliminable Diketopyrrolopyrrole Derivative (Part 5)
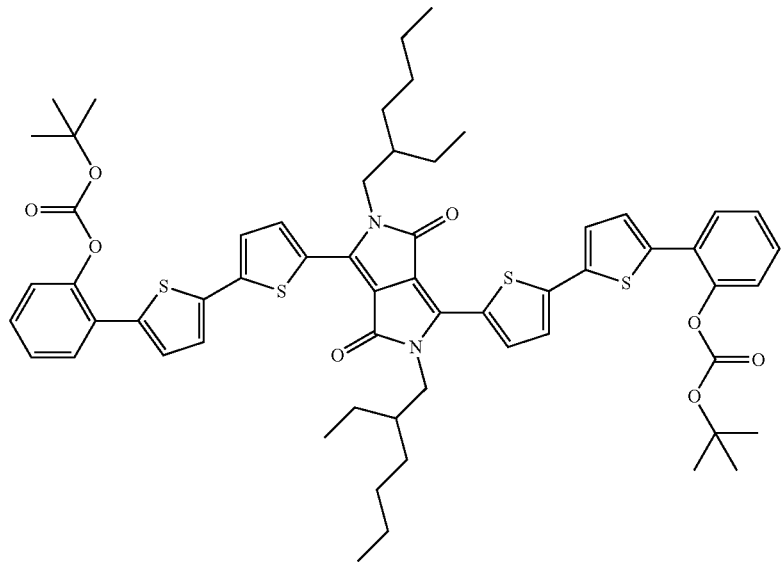 [SMILES: CCCCC(CC)CN1C(=O)C2=C(c3ccc(-c4ccc(-c5ccccc5OC(=O)OC(C)(C)C)s4)s3)N(CC(CC)CCCC)C(=O)C2=C1c1ccc(-c2ccc(-c3ccccc3OC(=O)OC(C)(C)C)s2)s1]
Substituent-eliminable Derivative No. 15
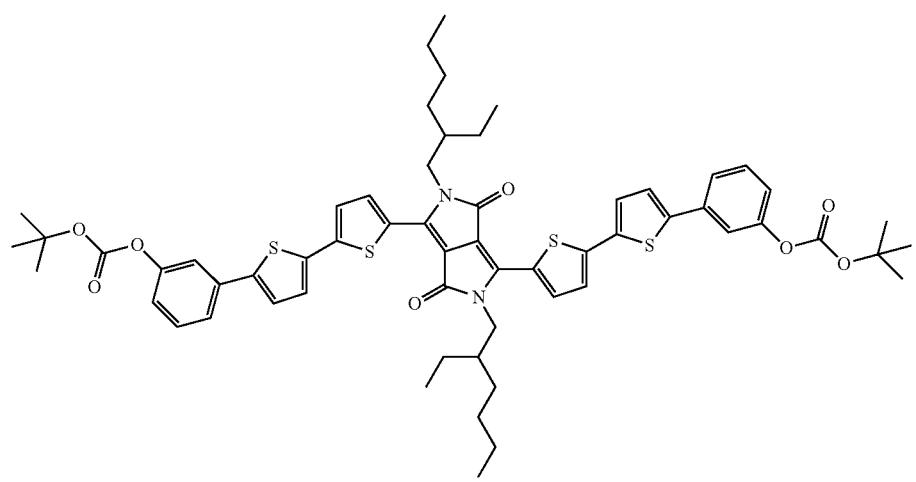 [SMILES: CCCCC(CC)CN1C(=O)C2=C(c3ccc(-c4ccc(-c5cccc(OC(=O)OC(C)(C)C)c5)s4)s3)N(CC(CC)CCCC)C(=O)C2=C1c1ccc(-c2ccc(-c3cccc(OC(=O)OC(C)(C)C)c3)s2)s1]
Substituent-eliminable Derivative No. 16

TABLE 1-6

Examples of Substituent-eliminable Diketopyrrolopyrrole Derivative (Part 6)

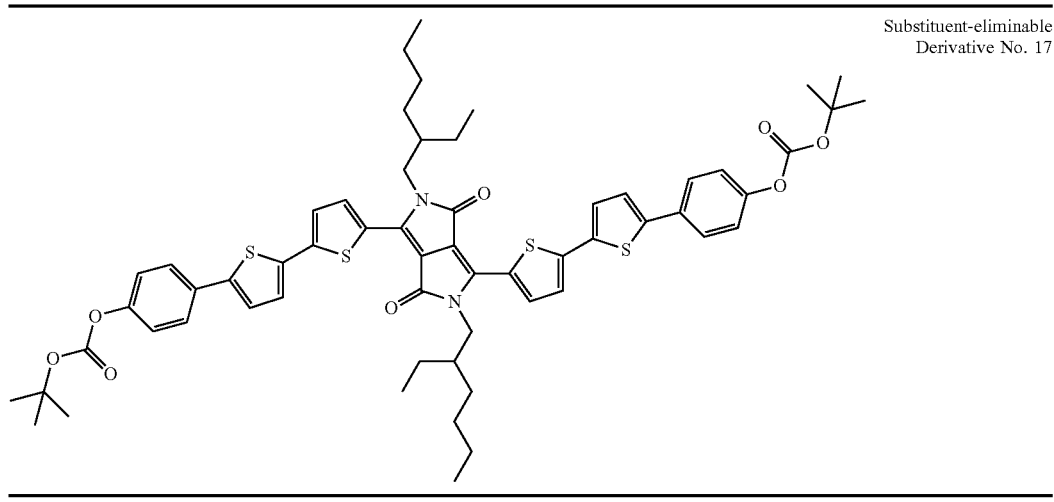

Substituent-eliminable Derivative No. 17

By giving energy such as heat (giving or applying external stimuli) to the substituent-eliminable diketopyrrolopyrrole derivative to invoke an elimination reaction, to be described in detail later, the specific compound from which the eliminable group has been eliminated will be obtained.

Specific examples of the specific diketopyrrolopyrrole compound obtainable from the above-described substituent-eliminable diketopyrrolopyrrole derivatives are listed below, but are not limited thereto.

TABLE 2-1

Examples of Specific Diketopyrrolopyrrole Compound (Part 1)

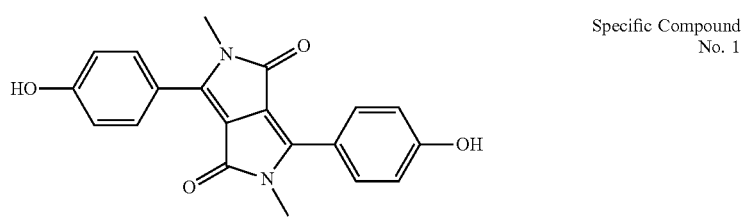

Specific Compound No. 1

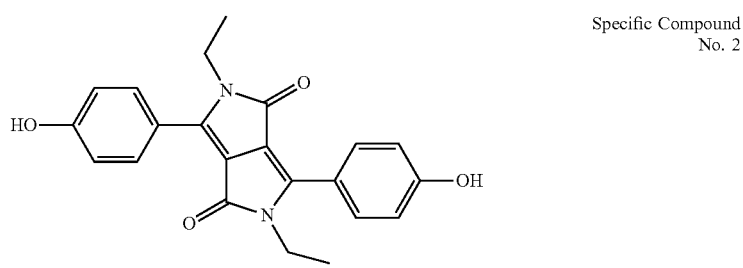

Specific Compound No. 2

TABLE 2-1-continued
Examples of Specific Diketopyrrolopyrrole Compound (Part 1)
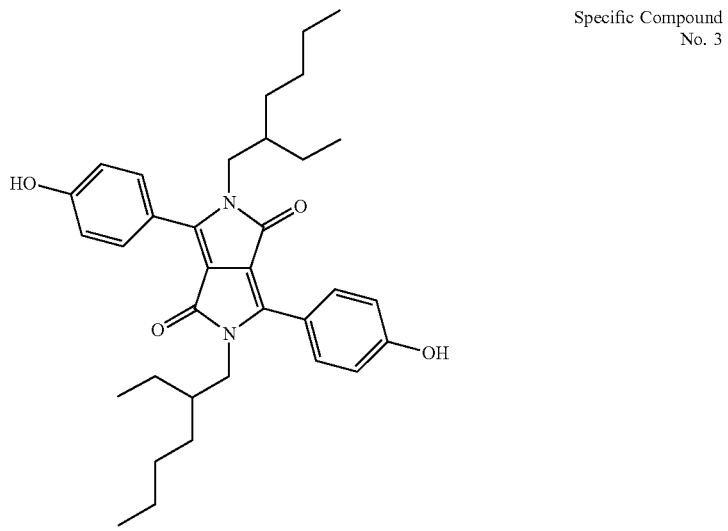
Specific Compound No. 3
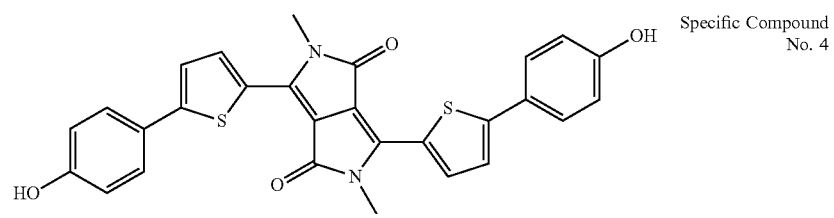
Specific Compound No. 4
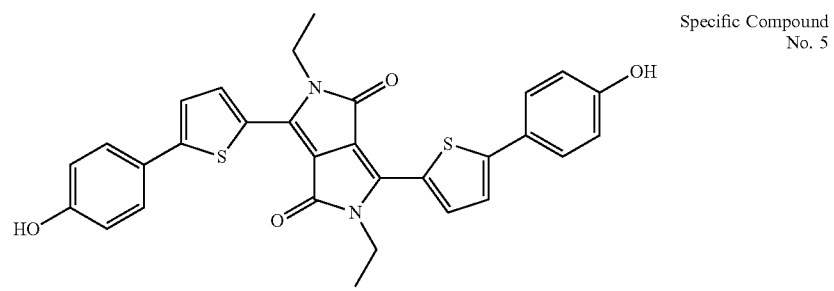
Specific Compound No. 5

TABLE 2-2
Examples of Specific Diketopyrrolopyrrole Compound (Part 2)
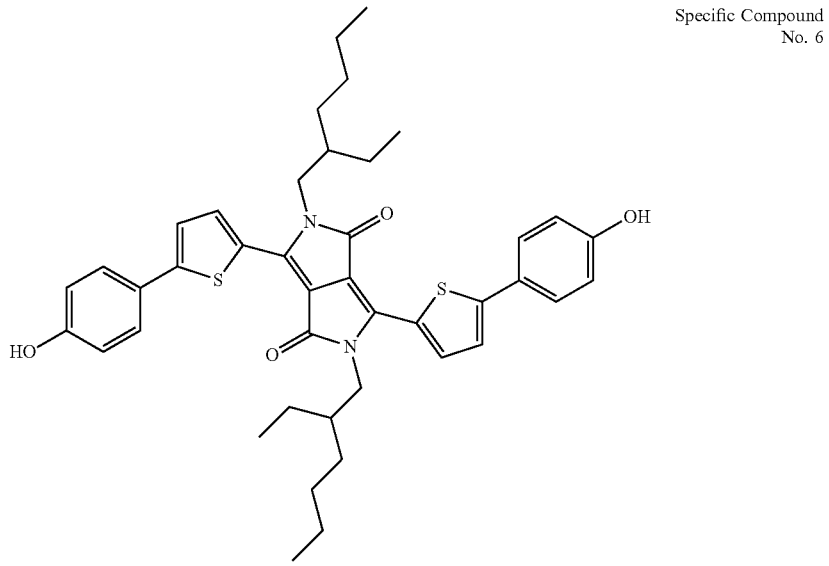
Specific Compound No. 6
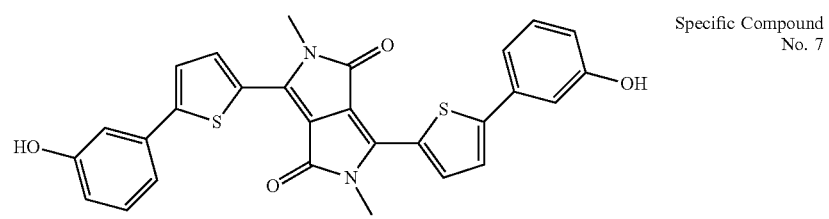
Specific Compound No. 7
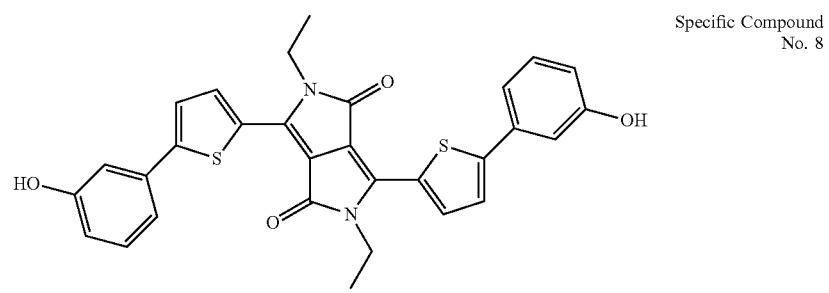
Specific Compound No. 8

TABLE 2-2-continued
Examples of Specific Diketopyrrolopyrrole Compound (Part 2)
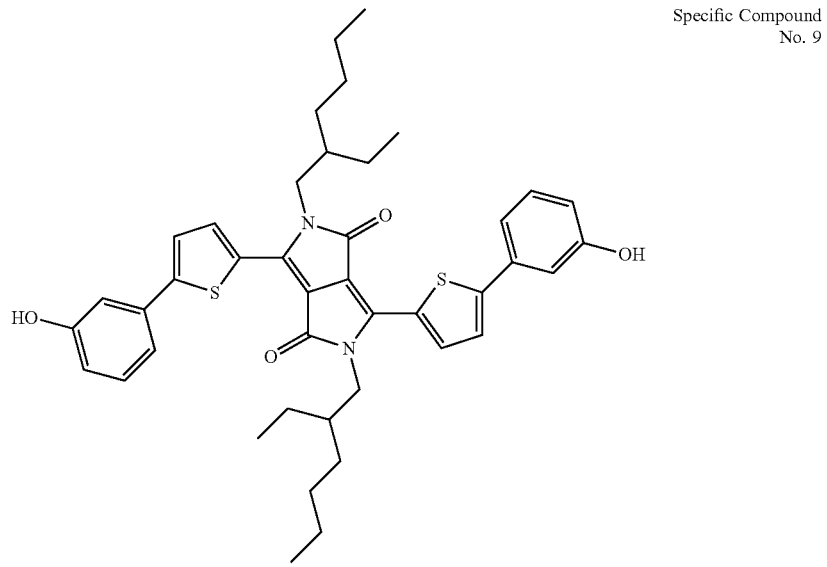
Specific Compound No. 9
TABLE 2-3
Examples of Specific Diketopyrrolopyrrole Compound (Part 3)
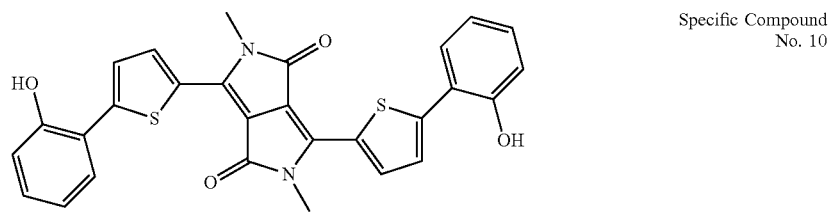
Specific Compound No. 10
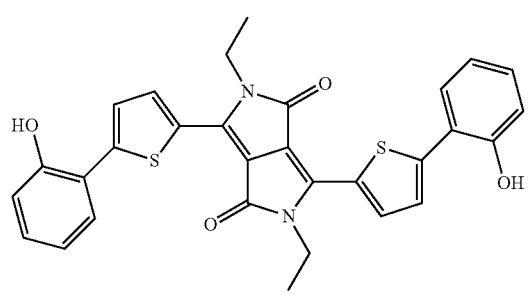 [SMILES: CCN1C(=O)C2=C(c3ccc(-c4ccccc4O)s3)N(CC)C(=O)C2=C1c1ccc(-c2ccccc2O)s1]
Specific Compound No. 11

TABLE 2-3-continued
Examples of Specific Diketopyrrolopyrrole Compound (Part 3)
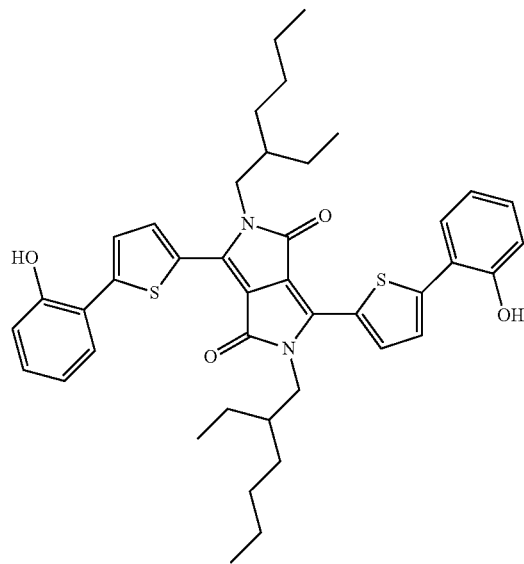 [SMILES: CCCCC(CC)CN1C(=O)C2=C(c3ccc(-c4ccccc4O)s3)N(CC(CC)CCCC)C(=O)C2=C1c1ccc(-c2ccccc2O)s1]
Specific Compound No. 12
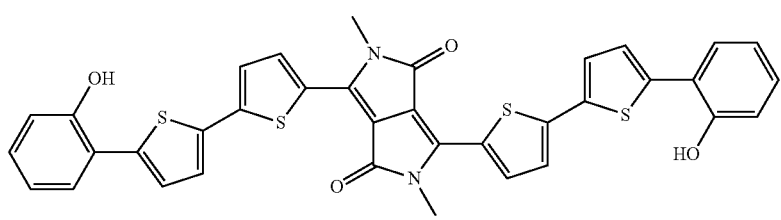 [SMILES: CN1C(=O)C2=C(c3ccc(-c4ccc(-c5ccccc5O)s4)s3)N(C)C(=O)C2=C1c1ccc(-c2ccc(-c3ccccc3O)s2)s1]
Specific Compound No. 13
TABLE 2-4
Examples of Specific Diketopyrrolopyrrole Compound (Part 4)
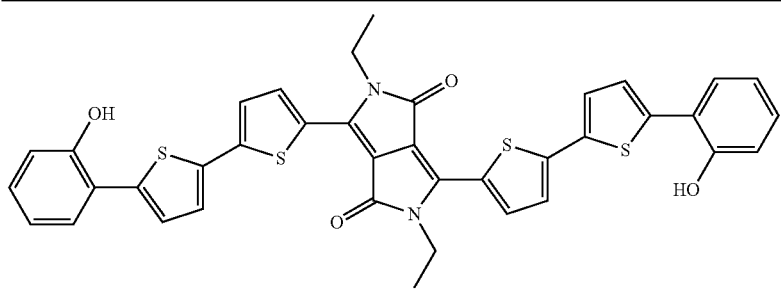
Specific Compound No. 14

TABLE 2-4-continued
Examples of Specific Diketopyrrolopyrrole Compound (Part 4)
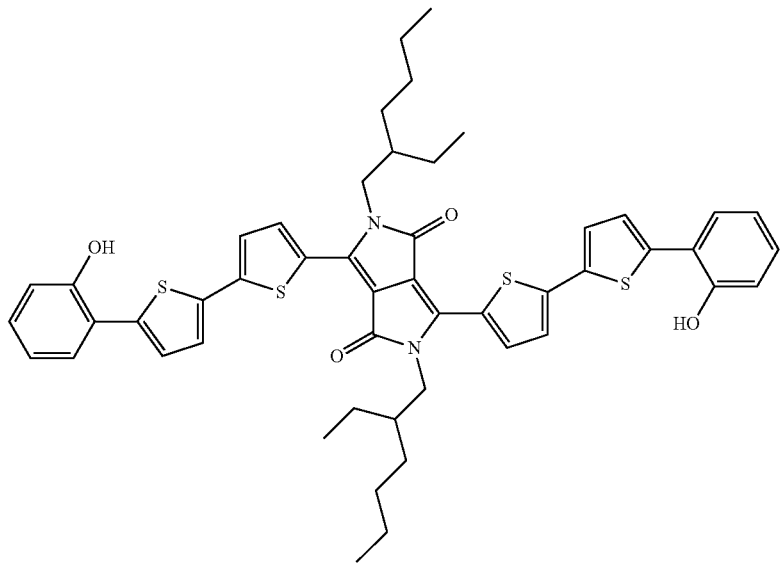 [SMILES: CCCCC(CC)CN1C(=O)C2=C(c3ccc(-c4ccc(-c5ccccc5O)s4)s3)N(CC(CC)CCCC)C(=O)C2=C1c1ccc(-c2ccc(-c3ccccc3O)s2)s1]
Specific Compound No. 15
TABLE 2-5
Examples of Specific Diketopyrrolopyrrole Compound (Part 5)
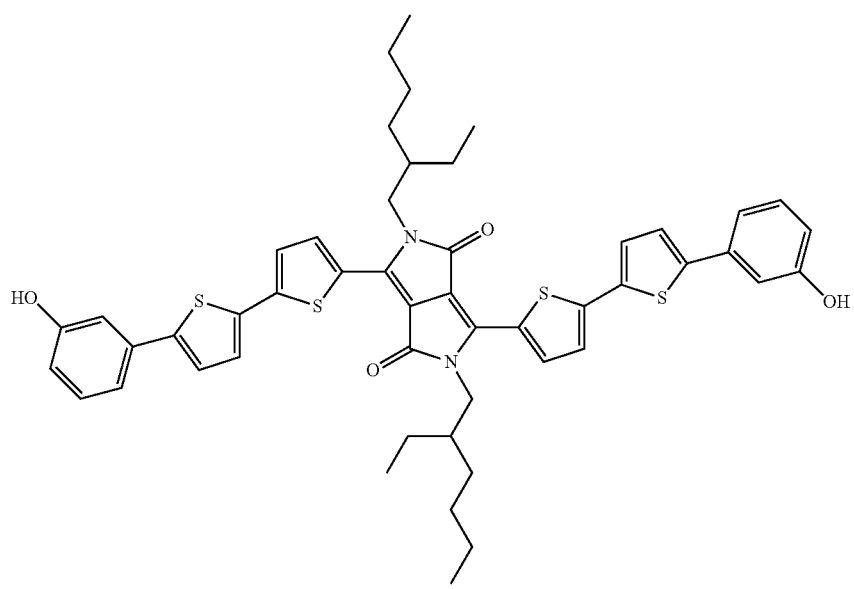 [SMILES: CCCCC(CC)CN1C(=O)C2=C(c3ccc(-c4ccc(-c5cccc(O)c5)s4)s3)N(CC(CC)CCCC)C(=O)C2=C1c1ccc(-c2ccc(-c3cccc(O)c3)s2)s1]
Specific Compound No. 16

TABLE 2-5-continued

Examples of Specific Diketopyrrolopyrrole Compound (Part 5)

Specific Compound No. 17

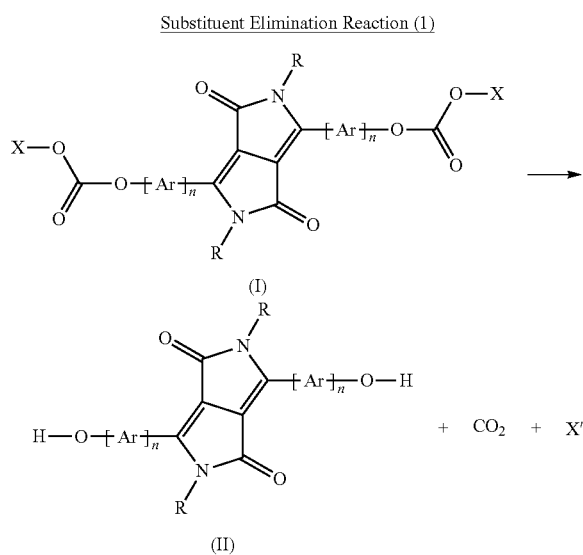

2, Manufacturing Method of N-Hydrogenated Diketopyrrolopyrrole Compound (Specific Compound) by Elimination Reaction of Substituent-Eliminable Diketopyrrolopyrrole Derivative (Substituent-Eliminable Derivative)

The above-described elimination reaction is described in detail below.

As described above, the substituent-eliminable derivative represented by the formula (I) is converted into the diketopyrrolopyrrole compound represented by the formula (II) upon application of energy.

Substituent Elimination Reaction (1)

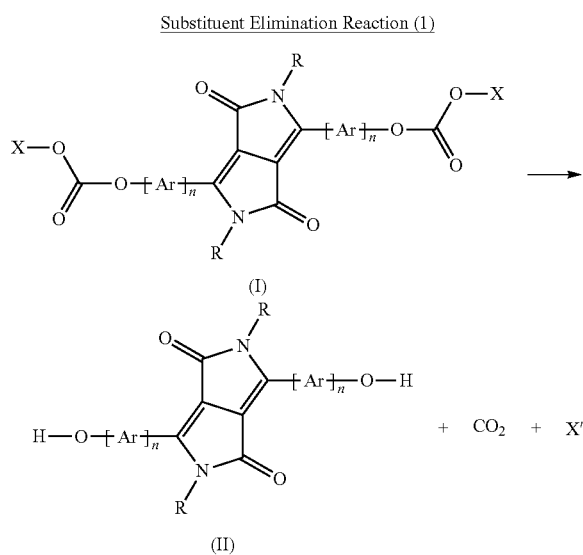

In the reaction scheme (1), representatives of R, X, Ar, and n are each described above and X' satisfies the formula: X'+H=X.

The group represented by the formula (IA), i.e., —COOX where X represents a substituted or unsubstituted alkyl group, is defined as the eliminable substituent to be eliminated from the substituent-eliminable diketopyrrolopyrrole derivative represented by the formula (I). The elimination component can be in either solid, liquid, or gaseous state. Given the ease of removal from the reaction system, the elimination component is preferably in a liquid or gaseous state, more preferably in a gaseous state at normal temperatures or at the elimination reaction temperature.

The elimination component preferably has a boiling point of 500° C. or less at atmospheric pressure (1,013 hPa). Given the ease of removal from the reaction system and the decomposition and sublimation temperatures of the resultant π-conjugate system, the boiling temperature is more preferably 300° C. or less, and most preferably 200° C. or less.

The following reaction scheme (2) represents an elimination reaction wherein X is tert-butyl group. The elimination reaction according to an embodiment of the present invention is not limited thereto.

Substituent Elimination Reaction (2)

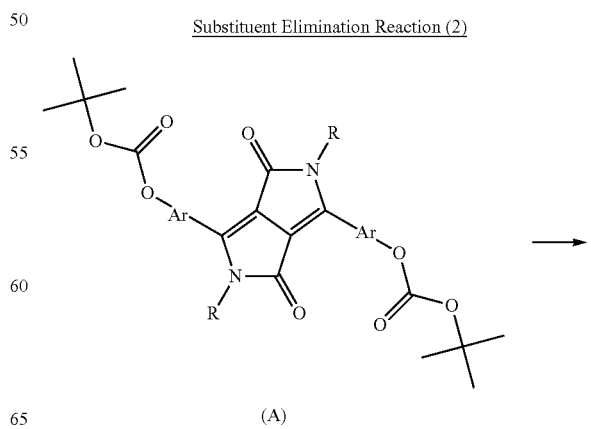

(A)

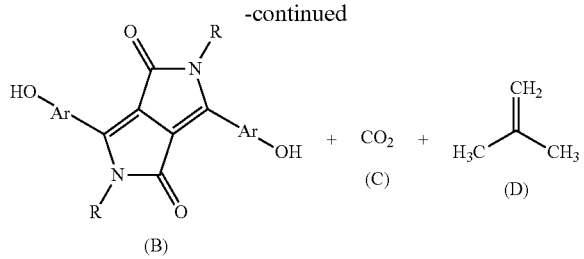

In the above reaction scheme (2), upon application of energy (heat), o-(t-butyloxycarbonyl)diketopyrrolopyrrole structure represented by formula (A) converts into a diketopyrrolopyrrole structure represented by formula (B) by eliminating carbon dioxide represented by formula (C) and isobutene represented by formula (D). Since carbon dioxide and isobutene are both in a gaseous state at normal temperatures and pressures, they are immediately discharged from the reaction system.

The kind of energy to be applied may be, for example, heat, light, and electromagnetic wave. In view of reactivity, yield, and the ease of post-treatment, heat or light is preferable, and heat is more preferable. The application of energy may be conducted in the presence of acid or base.

Depending on the structures of present functional groups, in many cases, the elimination reaction requires heat to progress in view of reaction rate and reactivity. Methods of applying heat for proceeding the elimination reaction includes, for example, heating on a substrate, heating in an oven, irradiation of microwaves, heating by converting light into heat with use of laser, and heating with use of photothermal layer, but are not limited thereto.

The heating temperature may be set within a range of from room temperature (approximately 25° C.) to 500° C. Determining the lower limit temperature in view of thermal stability of materials and boiling point of elimination components, and the upper limit temperature in view of energy efficiency, existence ratio, decomposition and sublimation properties of the resulting converted compound, the heating temperature is preferably set within a range of from 40 to 500° C. Further, in view of thermal stability in synthesizing the substituent-eliminable derivative, the heating temperature is set more preferably from 60 to 500° C. and most preferably from 80 to 400° C.

With regard to the heating time, the higher the temperature, the shorter the reaction time. In other words, as the temperature lowers, the time required for the elimination reaction gets longer. Depending on reactivity and quantity of the substituent-eliminable derivative, the heating time is typically 0.5 to 120 minutes, preferably 1 to 60 minutes, and more preferably 1 to 30 minutes.

Methods of applying light energy as an external stimulus include, for example, irradiation of light emitted from infrared ray lamp or light which will be absorbed by the compound (e.g., irradiation of light having a wavelength of 405 nm or less). Semiconductor laser can be used for such irradiation.

For example, near-infrared laser light (i.e., typically laser light having a wavelength around 780 nm), visible laser light (i.e., typically laser light having a wavelength of from 630 to 680 nm), and laser light having a wavelength of from 390 to 440 nm are preferred. Among these lights, laser light having a wavelength of from 390 to 440 nm is most preferred, such as semiconductor laser light having an oscillation wavelength of 440 nm or less. Preferred light sources include blue-violet semiconductor laser light having an oscillation wavelength of from 390 to 440 nm (more preferably from 390 to 415 nm) and blue-violet SHG laser light having a central oscillation wavelength of 425 nm obtained by reducing by half the central oscillation wavelength of 850 nm of infrared semiconductor laser light with an optical waveguide device.

In the elimination reaction of the eliminable substituent, an acid or base will act as a catalyst, making it possible to conduct the conversion at lower temperatures. An acid or base may be introduced to the reaction system by, for example: directly adding an acid or base to the substituent-eliminable derivative; firstly dissolving an acid or base in a solvent to prepare a solution and secondly adding the solution to the substituent-eliminable derivative; vaporizing an acid or base and conducting heat treatment in the atmosphere; or adding a photo-acid generating agent or photo-base generating agent to the reaction system and emitting light thereto to generate an acid or base.

Specific examples of the acid include, but are not limited to, hydrochloric acid, nitric acid, sulfuric acid, acetic acid, trifluoroacetic acid, trifluoromethane sulfonic acid, 3,3,3-trifluoropropionic acid, formic acid, phosphoric acid, and 2-butyloctanoic acid.

Specific examples of the photo-acid generating agent include, but are not limited to, ionic generating agents such as sulfonium salts and iodonium salts; and nonionic generating agents such as imide sulfonate, oxime sulfonate, disulfonyl diazomethane, and nitrobenzyl sulfonate, Specific examples of the base include, but are not limited to, hydroxides such as sodium hydroxide and potassium hydroxide; carbonates such as sodium hydrogen carbonate, sodium carbonate, and potassium carbonate; amines such as triethylamine and pyridine; and amidines such as diazabicyclo undecene and diazabicyclo nonene.

Specific examples of the photo-base generating agent include, but are not limited to, carbamates, acyl oximes, and ammonium salts.

In view of the ease of removal from the reaction system after the reaction has been completed, the elimination reaction is preferably conducted in the atmosphere of a volatile acid or base.

The elimination reaction can be conducted under atmospheric pressure with or without a catalyst but is preferably conducted in an inert gas (e.g., nitrogen, argon) atmosphere or under reduced pressures so as to remove effects from side reactions of (e.g., oxidation) and moisture and to promote discharge of the elimination components from the reaction system.

3. Method of Manufacturing Substituent-Eliminable Derivative

The substituent-eliminable derivative according to an embodiment of the present invention has a diketopyrrolopyrrole skeleton and an eliminable substituent, as described above.

Because the eliminable substituent is bulky, the substituent-eliminable derivative has poor crystallinity. On the other hand, a molecule with such a structure has good solubility. Thus, a poor-crystallinity or amorphous film is easily obtainable by applying a solution of the substituent-eliminable diketopyrrolopyrrole derivative.

Methods of forming the diketopyrrolopyrrole skeleton and eliminable substituent are explained below.

Scheme (i)

(First Step)

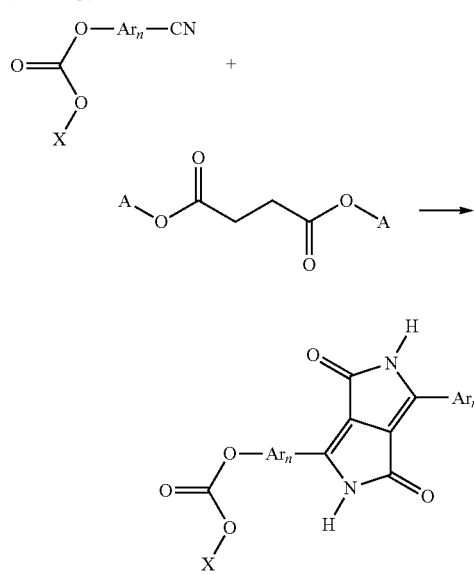

First, as shown in the scheme (i), a nitrile body is allowed to react with a disuccinate in the presence of a base.

Scheme (ii)

(Second Step)

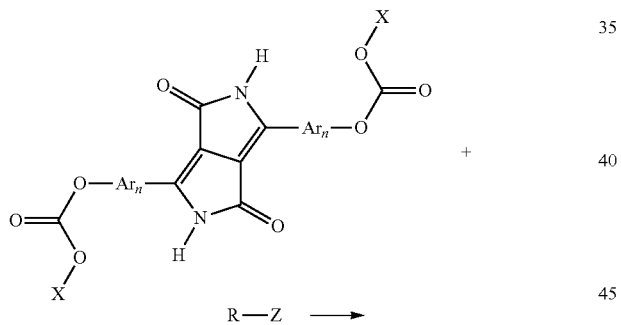

Next, the resulting compound is allowed to react with a halogenated compound in the presence of a base to obtain a substituent-eliminable diketopyrrolopyrrole compound in which nitrogen atoms are substituted, represented by the formula (I).

The following is another example of forming the diketopyrrolopyrrole skeleton and eliminable substituent.

(Scheme iii)

(First Step: Reaction between a nitrile and a disuccinate, similar to Scheme (i))

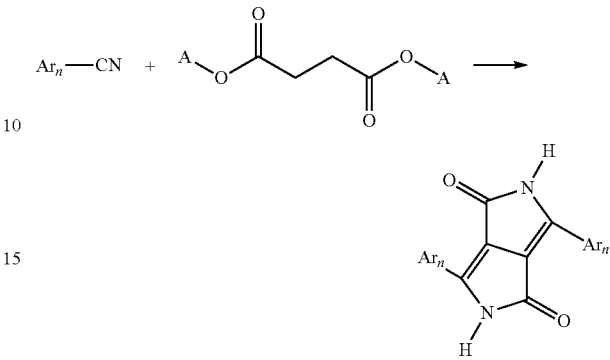

(Scheme (iv))

(Second Step: Substitution Reaction of Nitrogen Atoms Similar to Scheme ii))

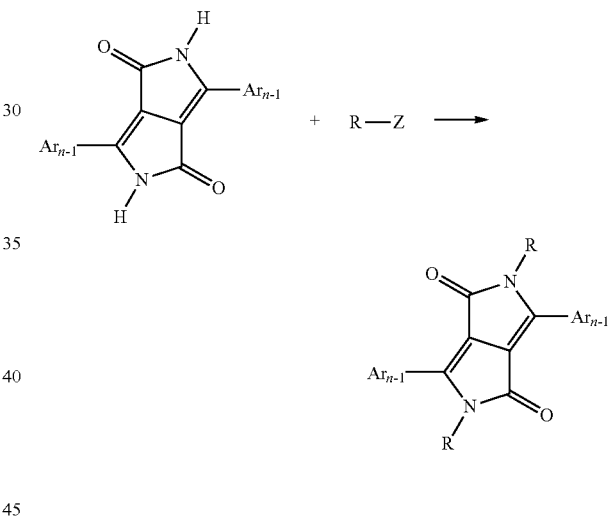

(Scheme (v))

(Third Step: Bromination with Brominating Agent)

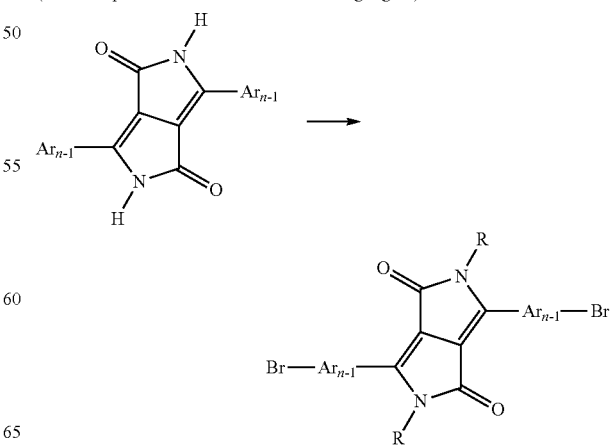

(Scheme vi)

(Fourth Step: Cross-coupling Reaction)

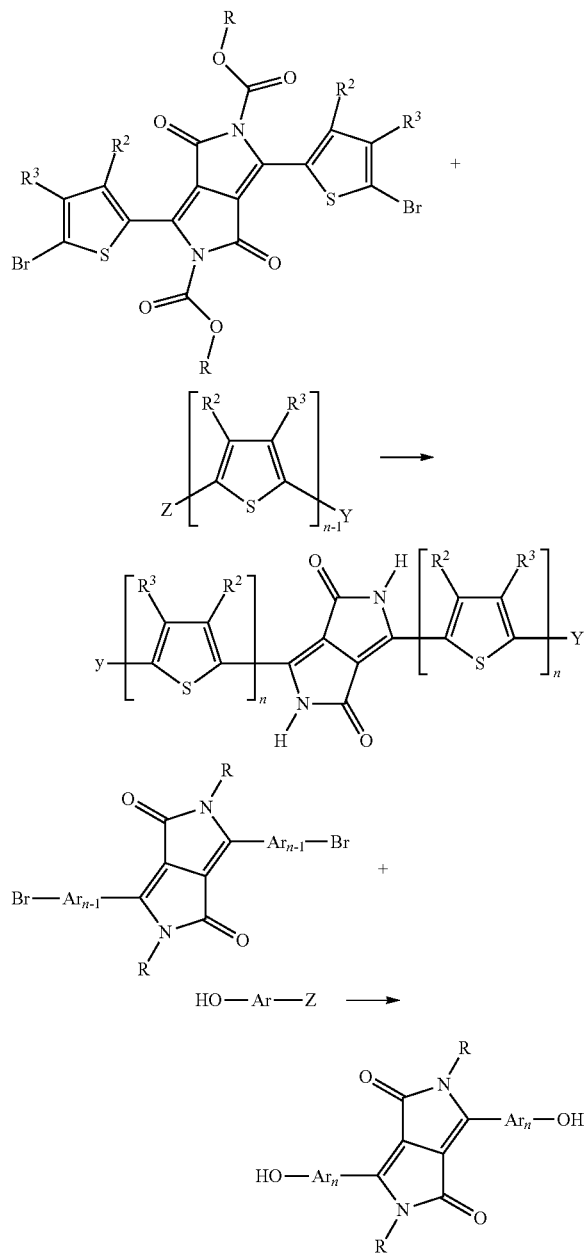

(Scheme vii)

(Fifth Step: Formation of Dicarbonine Acid Compound)

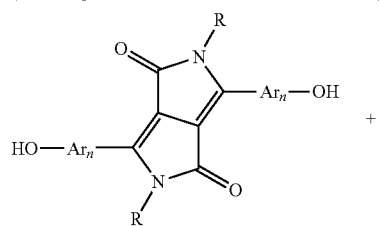

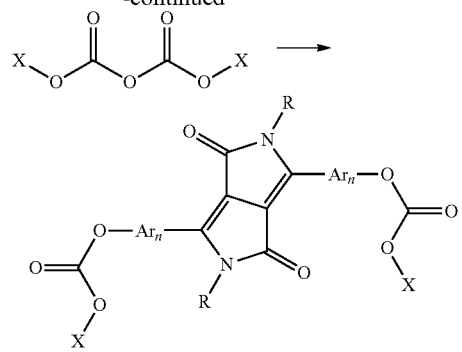

In the above schemes (i) to (vii), A and X independently represents an alkyl group having a carbon number of from 1 to 10, such as methyl group, ethyl group, n-propyl group, iso-propyl group, and t-butyl group. Schemes (iii) and (iv) proceed in the same manner as schemes (i) and (ii).

The reaction of scheme (v) proceeds with use of a brominating agent such as bromine and N-bromosuccinimide.

Scheme (vi) represents various cross-coupling reactions between aromatic groups and/or heteroaromatic groups in the presence of a known metal catalyst. Z represents a group derived from a boronic acid or tin.

Examples of Z derived from boronic acids are shown below.

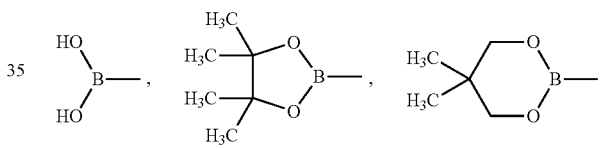

An example of Z derived from tin is shown below:

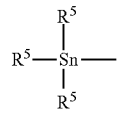

wherein R5 represents an alkyl group having a carbon number of from 1 to 10.

As an example of cross-coupling reactions using metal catalyst, the Suzuki coupling reaction is explained in detail below.

The Suzuki coupling reaction takes place between a halide and a boron compound. Usable halides include aryl halides and the halide is preferably iodide or bromide in view of reactivity. Usable boron compounds include aryl boron compounds, such as aryl boronic acids, aryl boronic acid esters, and aryl boronic acid salts. Among these compounds, aryl boronic acid esters are preferable for the following reasons: they do not produce trimeric anhydride (boroxine), unlike aryl boronic acids; they have high crystallinity; and that they are easy to purify. An aryl boronic acid ester can be synthesized by one of the following methods, for example.

(i) Allow an aryl boronic acid to react with an alkyl diol n an anhydrous organic solvent under heat.

(ii) Metalize the halogen in an aryl halide and then add an alkoxyborone ester thereto.

(iii) Prepare Grignard reagent of an aryl halide and then add an alkoxyborone ester thereto.

(iv) Allow an aryl halide to react with bis(pinacolato) diborone or bis(neopentyl glycolato)diborone in the presence of a palladium catalyst under heat. Specific examples of the palladium catalyst include, but are not limited to, $Pd(PPh_3)_4$, $PdCl_2(PPh_3)_2$, $Pd(OAc)_2$, $PdCl_2$, and palladium carbon having triphenyl phosphine as a ligand. $Pd(PPh_3)_4$ is most widely used.

The presence of a base is necessary for the Suzuki coupling reaction. Relatively weak bases, such as $Na_2CO_3$, $NaHCO_3$ and $K_2CO_3$, bring good results. In a case in which the reaction is under the effect of steric hindrance, strong bases such as $Ba(OH)_2$ and $K_3PO_4$ are effective. Depending on the kind of reactive substrates, caustic soda is also effective in some cases.

Additionally, caustic potash and the following metal alkoxides are also usable: potassium t-butoxide, sodium t-butoxide, lithium t-butoxide, potassium 2-methyl-2-butoxide, sodium 2-methyl-2-butoxide, sodium methoxide, sodium ethoxide, potassium methoxide, and potassium ethoxide.

To make the reaction more smoothly proceed, phase-transfer catalysts are also usable. Specific preferred examples of the phase-transfer catalysts include tetraalkyl ammonium halides, tetraalkyl ammonium hydrogen sulfates, and tetraalkyl ammonium hydroxides. More specifically, tetra-n-butyl ammonium halide, benzyl trimethyl ammonium halide, and tricaprylyl methyl ammonium chloride are preferable.

The reaction may proceed under the atmospheric air but is preferably under an inert gas atmosphere, such as argon, so as not to deteriorate the catalyst.

In the reactions of schemes (i) to (vii), typical organic solvents are usable as the reaction solvent, such as alcohols and ethers (e.g., methanol, ethanol, isopropanol, butanol, 2-methoxyethanol, 1,2-dimethoxyethane, bis(2-methoxyethyl)ether), halogen solvents (e.g., chloroform, dichloromethane, 1,2-dichloroethane, carbon tetrachlotide, chlorobenzene, dichlorobenzene), cyclic ethers (e.g., dioxane, tetrahydrofuran), benzene, toluene, xylene, dimethylsulfoxide, N,N-dimethylformamide, N-methylpyrrolidone, and 1,3-dimethyl-2-imidazolidinone.

The reactions of schemes (i), (ii), (iii), (iv), and (vi) typically proceed at a temperature within a range from room temperature to 180° C., preferably from room temperature to 100° C. The reaction of scheme (v) typically proceeds at a temperature within a range from −50° C. to ±50° C., preferably from −10° C. to room temperature.

4. Application of Substituent-Eliminable Diketopyrrolopyrrole Derivative to Devices The organic semiconductor compound (specific compound) according to an embodiment of the present invention can be used for, for example, electronic devices, such as devices having two or more electrodes in which current to flow and voltage to be generated between the electrodes are controlled by means of electricity, light, magnetism, or chemical substances; and devices to generate light, electric field, and/or magnetic field by application of voltage or current.

Additionally, examples of the electronic devices further include elements to control current or voltage by application of voltage or current, elements to control voltage or current by application of magnetic field, and elements to control voltage or current by the action of chemical substances. Specific means for these controls include, but are not limited to, rectification, switching, amplification, and oscillation.

Specific examples of the corresponding devices already having been put into practice use with use of inorganic semiconductors, such as silicone, include, for example, resistors, rectifiers (diodes), switching elements (transistors, thyristors), amplifying elements (transistors), memory elements, chemical sensors, and devices in which the above elements are combined or integrated. Specific examples of the corresponding devices further include solar cells to generate electromotive force by light, photodiodes to generate photocurrent, and photonic devices such as phototransistor.

FIG. 1 is a schematic view of an example of a solar cell. This solar cell may be manufactured by, first, forming a positive electrode 2 of a conductive metallic material on a transparent substrate 1 such as glass. The positive electrode 2 can be formed by means of vacuum evaporation, etc. A positive hole extracting layer 3 may be optionally formed on the positive electrode 2. The positive hole extracting layer 3 is formed of a p-type semiconductor material by a coating method, etc. The positive hole extracting layer 3 is optionally and preferably subjected to annealing treatment by exposure to solvent vapor under the solvent atmosphere or by heating.

On the positive hole extracting layer 3, a mixed layer 4 is formed. The mixed layer 4 consists of a p-type semiconductor material that includes at least the substituent-eliminable diketopyrrolopyrrole derivative according to an embodiment of the present invention and an n-type semiconductor material. The mixed layer 4 can be formed by a coating method. The mixed layer 4 is also preferably subjected to annealing treatment by exposure to solvent vapor or by heating. An electron extracting layer 5 can be formed of an n-type semiconductor material by means of a dry film formation method or a wet film formation method.

The electron extracting layer 5 is also preferably subjected to annealing treatment by exposure to solvent vapor or by healing. Formation of the positive hole extracting layer 3 and/or electron extracting layer 5 is optional and not necessary. A negative electrode 6 is formed on the electron extracting layer 5. In the same manner as the positive electrode 2, the negative electrode 6 is formed of a conductive material by means of vacuum evaporation, etc.

EXAMPLES

Having generally described this invention, further understanding can be obtained by reference to certain specific examples which are provided herein for the purpose of illustration only and are not intended to be limiting.

First, intermediates of specific compounds used in the following examples and comparative examples are synthesized.

In the following synthesis examples and examples, compounds are identified by mass spectrometry with an instrument LCQ Fleet from Thermo Fischer Scientific Inc.

Synthesis Example 1

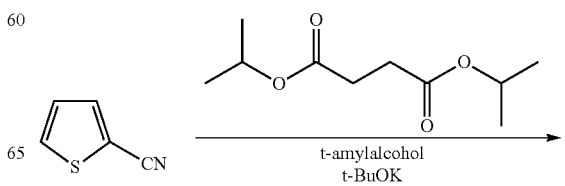

-continued

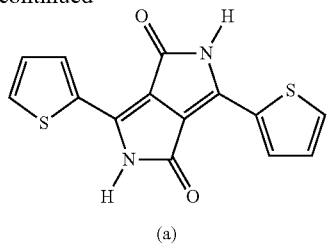

(a)

Charge a 200-ml four-neck flask with t-BuOK (19 g, 170 mmol) and t-amyl alcohol (70 ml) and heat to reflux under agitation.

Gradually drop a mixture of 2-cyanothiophene (10.9 g, 100 mmol) and diisopropyl succinate (9.63 g, 47.6 mmol) in the flask. After 3 hours of reflux, cool the flask content to 70° C. and add acetic acid (20 ml) and MeOH (20 ml) to the flask. After cooling to room temperature, filter the flask content with a glass filter to separate the precipitate. Wash the filter residue with methanol for 3 times and then dry it in a vacuum drier. Thus, a red solid (12.1 g, 42.2 mmol) represented by the formula (a) is prepared (at a yield of 50.8%). m/z=301.01 (M+H)

Synthesis Example 2

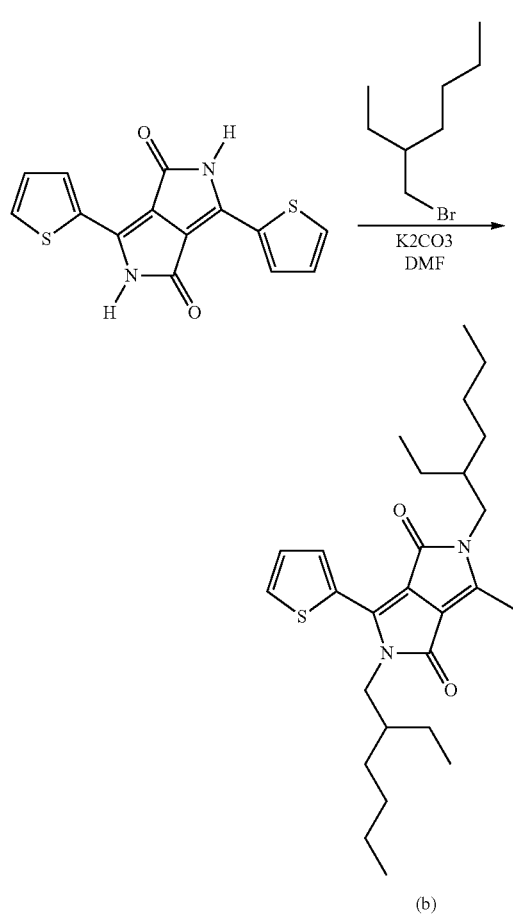

Charge a 500-ml eggplant-shape flask with the above-prepared compound (a) (5.0 g, 13.3 mmol), 2-ethylhexyl bromide (8.0 g, 41.6 mmol), dry DMF (100 ml), and potassium carbonate (6.0 g). Agitate the flask content all night long at 70° C. After distilling the solvent away under reduced pressures, add a mixed solvent of methanol and water (MeOH/water=1/1, 100 ml) to the flask. Separate the precipitate by filtration and purify it by a silica gel column chromatography (solvent: toluene). Thus, a red powder (4.5 g, 52.4%) is obtained. m/z=525.3 (M+H)

Synthesis Example 3

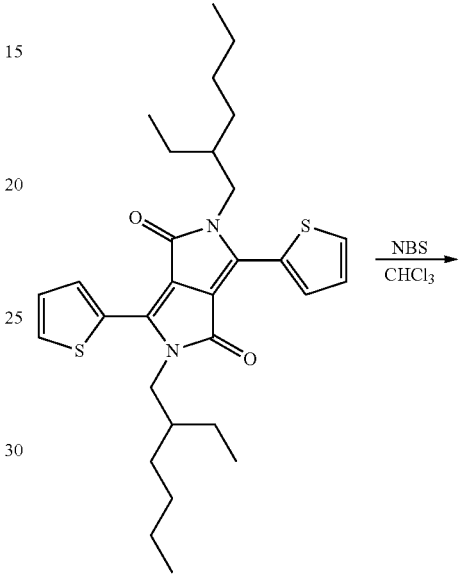

Charge a 500-ml eggplant-shape flask with the above-prepared compound (b) (3.0 g, 5.7 mmol), N-bromosuccinimide (2.5 g, 13.8 mmol), and chloroform (200 ml). Agitate the flask content for 12 hours at 0° C. under light shielding condition. After distilling the solvent away under reduced pressures, add MeOH (100 ml) to the flask. Separate the precipitate by filtration. Thus, a dark green powder (4.8 g, 71.0%) is obtained. m/z=683.1 (M+H)

Example 1

Substituent-Eliminable Derivative No. 6

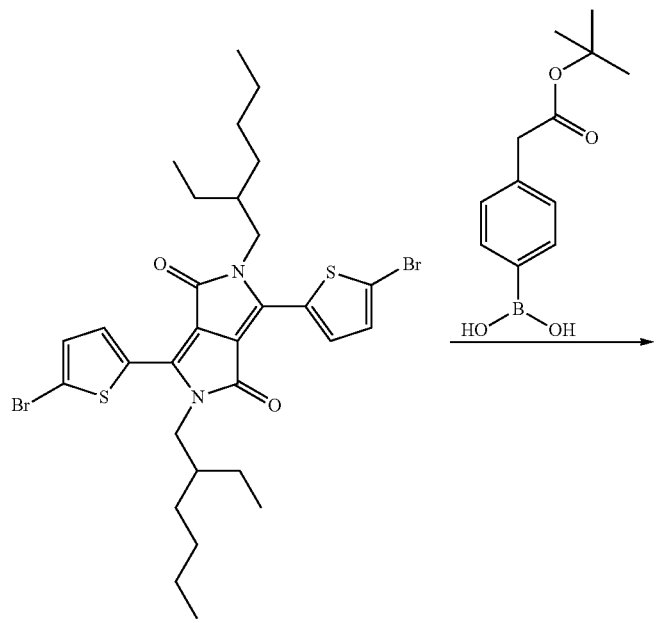

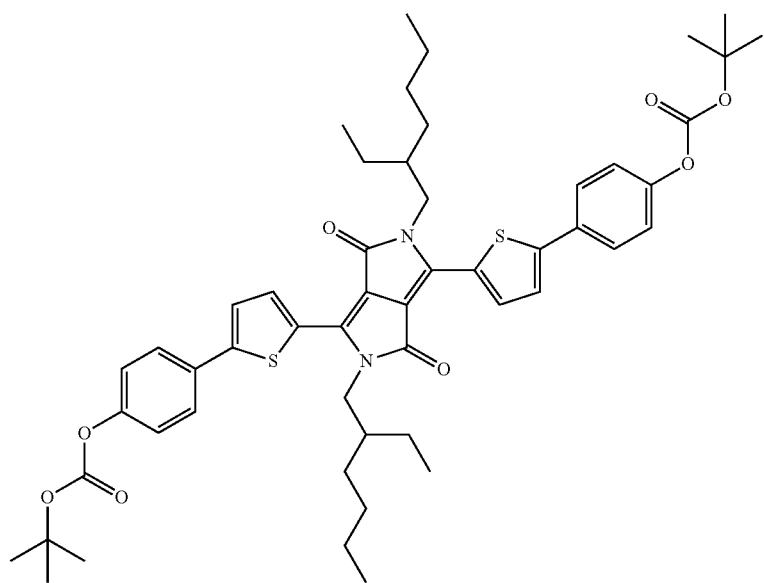

Charge a 100-ml four-neck flask with the above-prepared compound (c) (300 mg, 0.44 mmol), 4-(t-butyloxycarbonyl)-oxy-phenylboronic acid (214 mg, 0.9 mmol), Pd(P-tBu$_3$)$_4$ (22 mg, 4.4×10$^{-5}$ mol), K$_3$PO$_4$ (388 mg, 1.83 mmol), THF (10 ml), and water (2 ml), and reflux for 5 hours under Ar atmosphere. After cooling the flask content to room temperature, add methanol (100 ml) to the flask to cause precipitation. Separate the precipitate by filtration and purify it by a silica gel column chromatography (solvent: dichloromethane). Thus, a dark blue powder (170 mg, 42.3%) is obtained. m/z=904.2 (M+H)

Example 2

Substituent-Eliminable Derivative No. 9

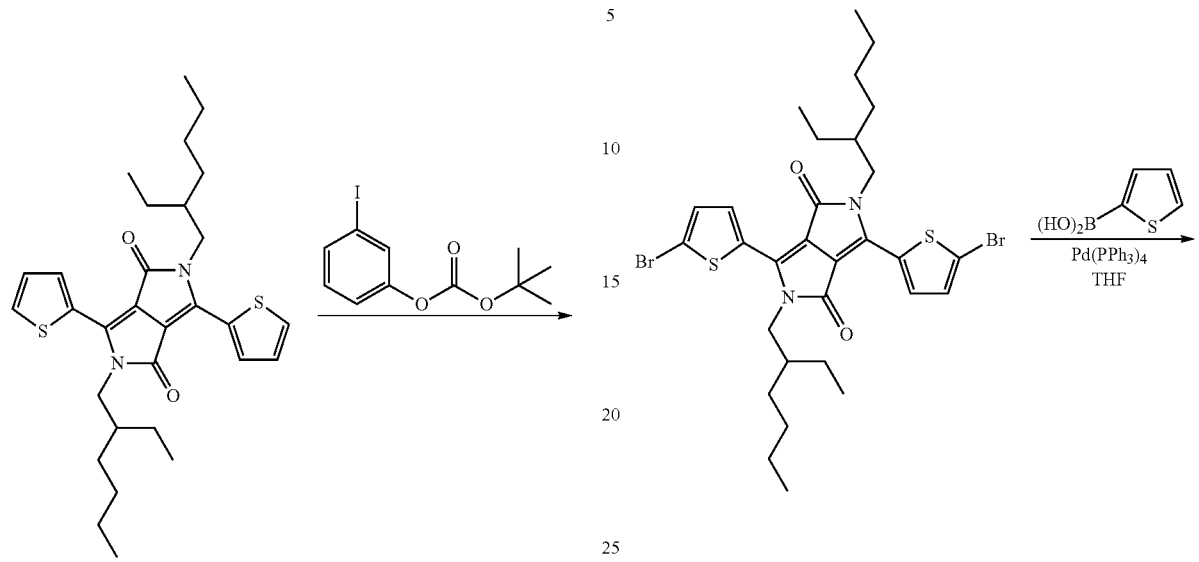

Synthesis Example 4

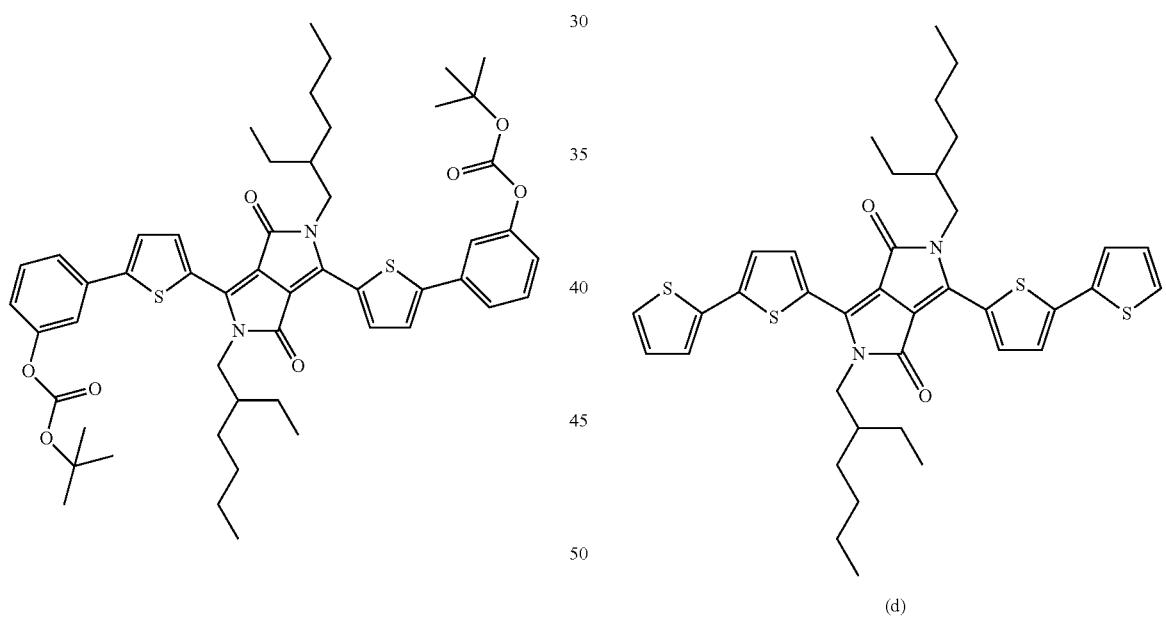

(d)

Charge a 100-ml four-neck flask with the above-prepared compound (b) (100 mg, 0.19 mmol), 4-(t-butyloxycarbonyl)-oxy-phenyl iodide (130 mg, 0.40 mmol), Pd(PPh$_3$)$_2$Cl$_2$ (14 mg, 1.9×10$^{-5}$ mol), KF (24 mg), AgNO$_3$ (71.4 mg), and DMSO (10 ml). Agitate the flask content at 80° C. for 5 hours under Ar atmosphere. After cooling the flask content to room temperature, add methanol (100 ml) to the flask to cause precipitation. Separate the precipitate by filtration and purify it by a silica gel column chromatography (solvent: dichloromethane). Thus, a dark blue powder (60 mg, 34.7%) is obtained. m/z=904.2 (M+H)

Charge a four-neck flask with the above-prepared compound (c) (1.5 g, 2.2 mmol), 2-thiophene boronic acid (630 mg, 4.9 mmol), Pd(PtBu$_3$)$_2$ (150 mg, 0.22 mmol), K$_3$PO$_4$ aqueous solution (10 ml, 20% by weight), and THF (50 nil), and reflux for 4 hours under Ar atmosphere. Cool the reaction liquid to room temperature and wash it with MeOH. Thus, a blue solid (1.3 g, 85%) is obtained. m/z=689.2 (M+H)

Example 3

Substituent-Eliminable Derivative No. 16

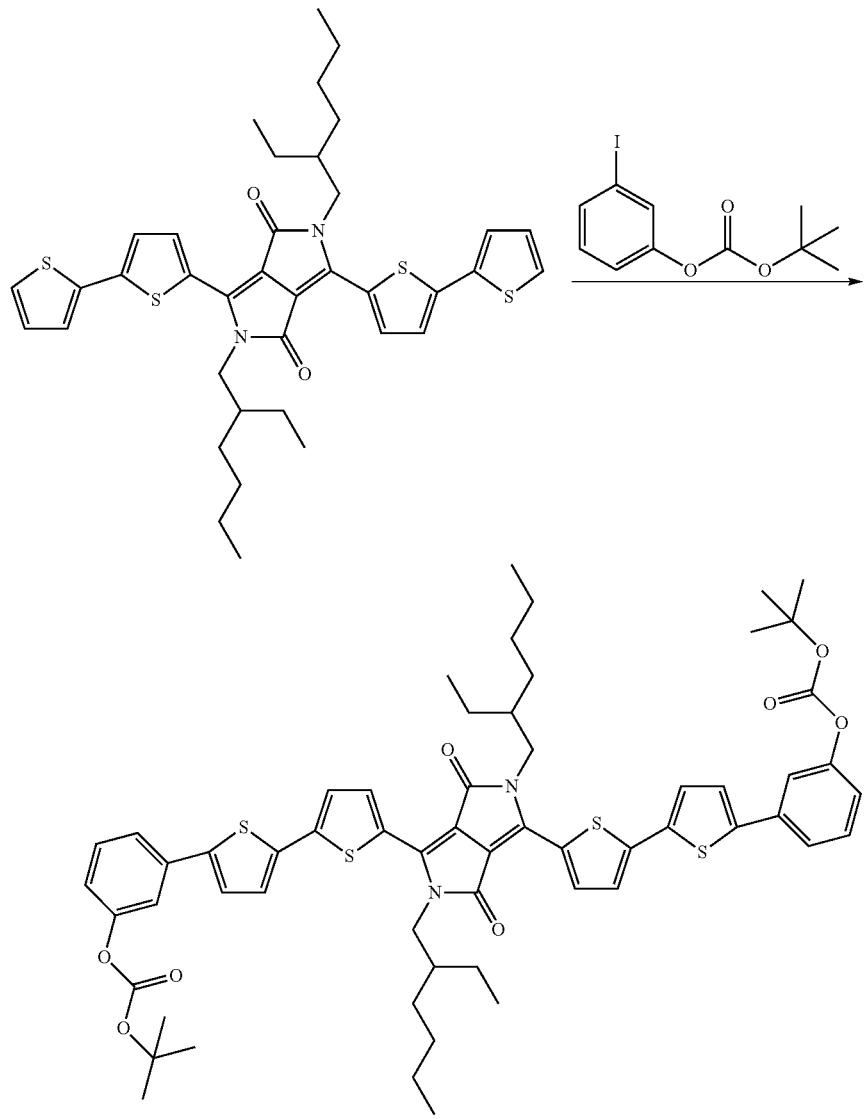

Charge a 100-ml four-neck flask with the above-prepared compound (d) (300 mg, 0.44 mmol), 4-t-butylcarbonyloxy phenyl iodide (560 mg, 1.74 mmol), Pd(PPh$_3$)$_2$Cl$_2$ (50 mg, 0.044 mol), KF (120 mg), AgNO$_3$ (360 mg), and DMSO (10 ml). Agitate the flask content at 80° C. for 5 hours under Ar atmosphere. After cooling the flask content to room temperature, add methanol (100 ml) to the flask to cause precipitation, Separate the precipitate by filtration and purify it by a silica gel column chromatography (solvent: dichloromethane). Thus, a dark blue powder (74 mg, 15.6%) is obtained. m/z=1073.4 (M+H)

Example 4

Conversion to Specific Compound 6

Figure 2:
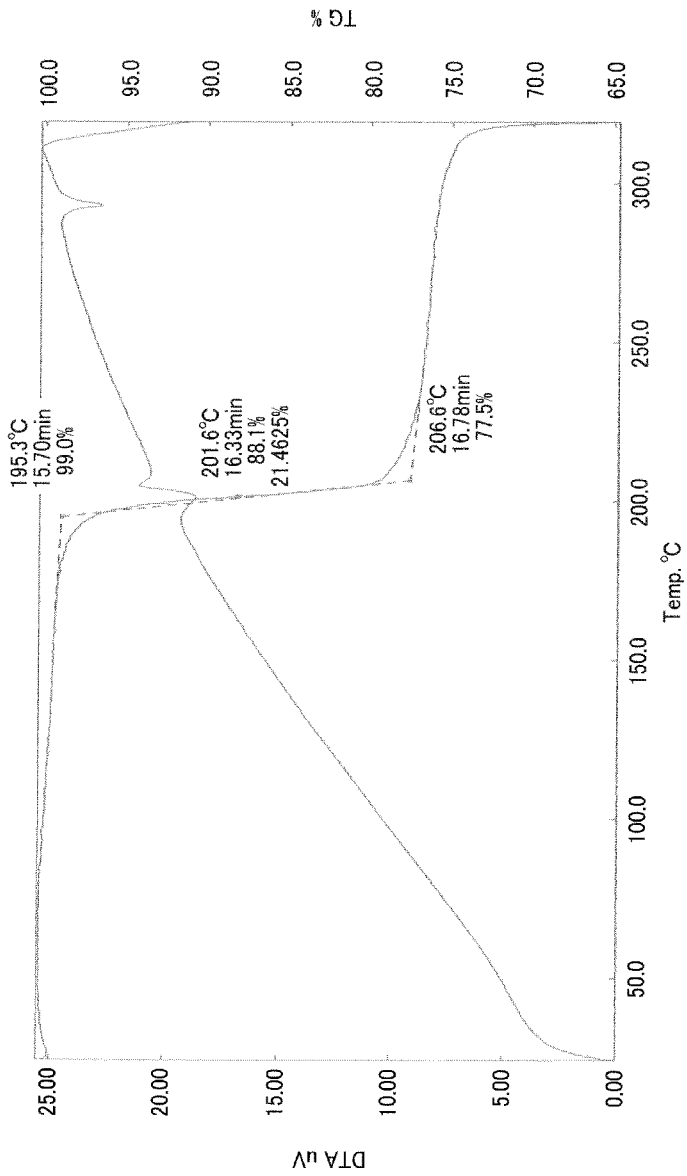
FIG. 2 is a graph showing the result of thermogravimetric measurement in Example 4.

Put the above-prepared substituent-eliminable derivative No. 6 (5 mg, 0.10 mmol) in an aluminum pan and heat it to 300° C. at a rate of 10° C./min with a thermal analysis instrument (EXSTAR 6200 from Seiko Instruments Inc.) under nitrogen atmosphere. Thus, a dark purple solid (3.8 mg) is obtained. m/z=704.1 (M+H). The thermogravimetric measurement result is shown in FIG. 2.

In the result, a 21.5% decrease in weight is observed within a range from 190 to 210° C. This amount of decrease in weight roughly corresponds with the amount of the elimination components, the ideal value of which is 22.1%. This result shows that the eliminable group has been eliminated by heat and the conversion has been completed.

Example 5

Conversion to Specific Compound 9

Put the above-prepared substituent-eliminable derivative No. 9 (5 mg, 5.5 mop in an aluminum pan and heat it to 250°

Figure 3:
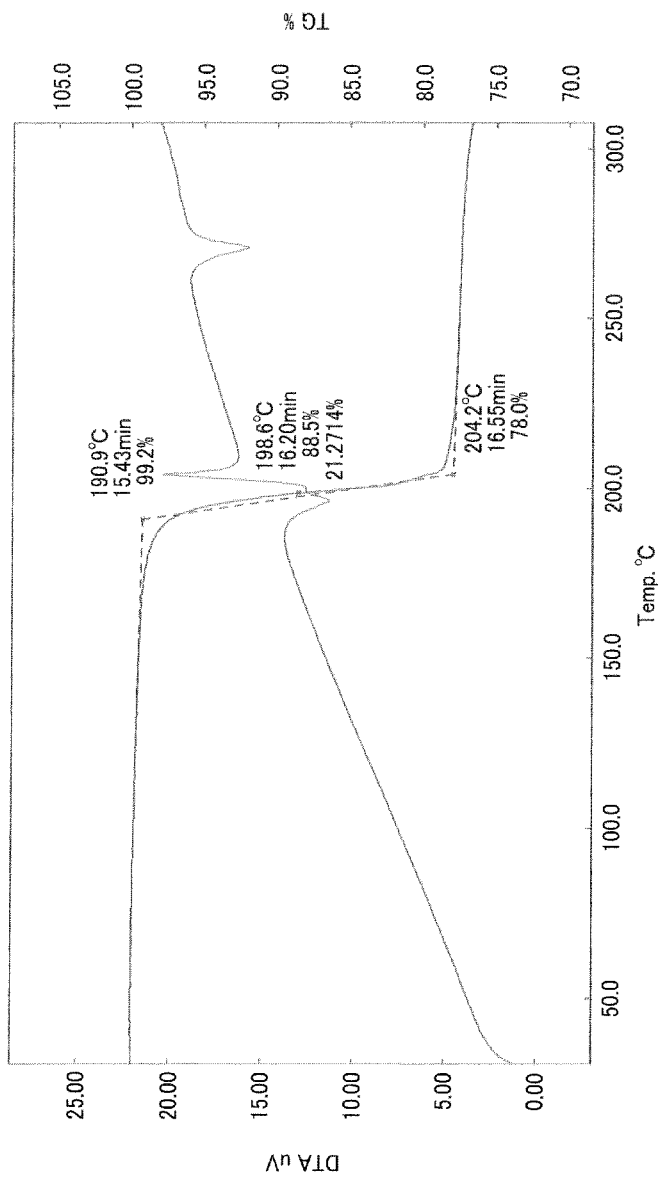
FIG. 3 is a graph showing the result of thermogravimetric measurement in Example 5.

C. at a rate of 20° C./min with a thermal analysis instrument (EXSTAR 6200 from Seiko Instruments Inc.) under nitrogen atmosphere. Thus, a dark purple solid (3.8 mg) is obtained. m/z=704.1 (M+H). The thermogravimetric measurement result is shown in FIG. 3.

In the result, a 21.2% decrease in weight is observed within a range from 190 to 210° C. This amount of decrease in weight roughly corresponds with the amount of the elimination components, the ideal value of which is 22.1%. This result shows that the eliminable group has been eliminated by heat and the conversion has been completed.

Example 6

Conversion to Specific Compound 16

Figure 4:
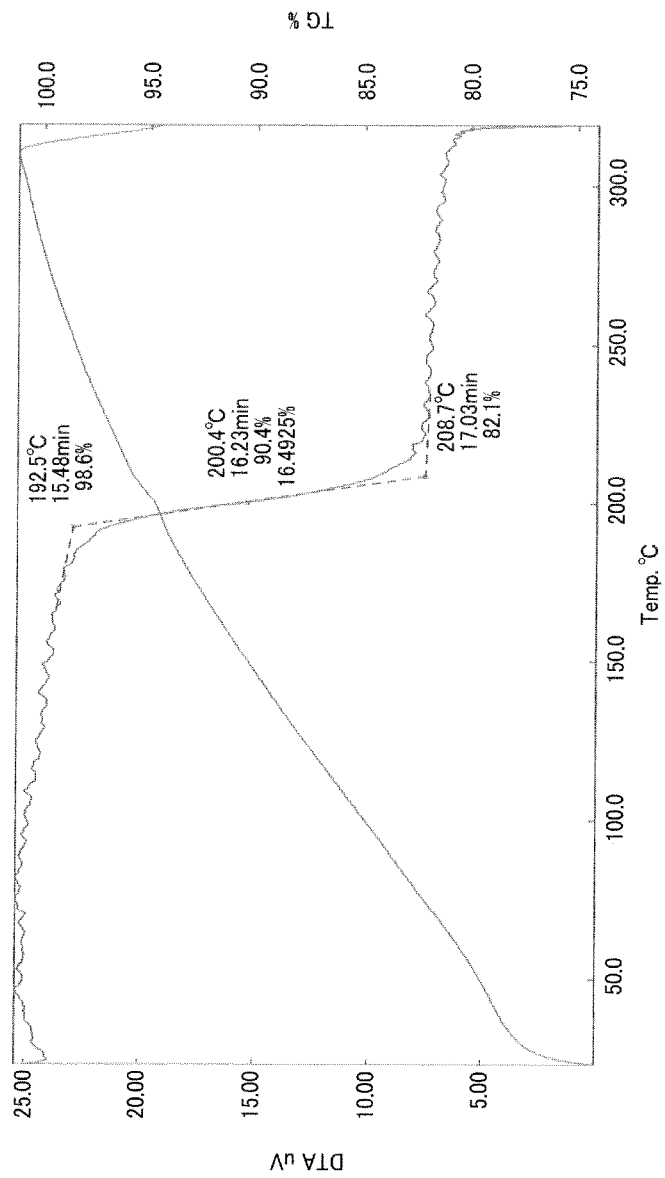
FIG. 4 is a graph showing the result of thermogravimetric measurement in Example 6.

Repeat the procedures in Example 4 except for replacing the substituent-eliminable derivative No. 6 with No. 16 (5 mg, 4.6 μmol). Thus, a dark purple specific compound (4.2 mg) is obtained. m/z=872.2 (M+H). The thermogravimetric measurement result is shown in FIG. 4.

In the result, a 18.5% decrease in weight is observed within a range from 190 to 210° C. This amount of decrease in weight roughly corresponds with the amount of the elimination components, the ideal value of which is 18.7%. This result shows that the eliminable group has been eliminated by heat and the conversion has been completed.

Example 7

Evaluation of Solubility: Making Organic Semiconductor Precursor into Ink

Add each of the compounds obtained in the above Examples 1-6 to each of toluene, THF, and chloroform until it gets undissolved. Agitate each solution for 10 minutes under solvent reflux, then cool it to room temperature, further agitate it for 1 hour, and allow it to stand for 16 hours. Filter the supernatant liquid with a 0.2-μm PTFE filter to obtain a saturated solution. Dry the solution under reduced pressures to calculate solubility of each compound against each solvent. The results are shown in Table 3. Evaluation criteria are as follows.
 A: Solubility is 0.5% by weight or more.
 B: Solubility is 0.05% by weight or more and less than 0.5% by weight.
 C: Solubility is 0.005% by weight or more and less than 0.05% by weight.
 D: Solubility is less than 0.005% by weight.

TABLE 3

| Compounds | Solvents | | |
|---|---|---|---|
| | THF | Toluene | Chloroform |
| Substituent-eliminable Derivative No. 6 | A | B | A |
| Substituent-eliminable Derivative No. 9 | A | A | A |
| Substituent-eliminable Derivative No. 16 | A | A | A |
| Specific Compound No. 6 | D | D | D |
| Specific Compound No. 9 | D | D | D |
| Specific Compound No. 16 | D | D | D |

The results in Table 3 show that the substituent-eliminable diketopyrrolopyrrole derivatives according to embodiments of the present invention have a solubility of 0.1% by weight or more in most of the solvents having different polarity. This means that there are various choices of solvents when they are used in coating processes.

Because of having high solubility, they can be applied to various film formation methods and printing methods, such as inkjet coating, spin coating, liquid casting, dip coating, screen printing, and gravure printing.

On the other hand, the specific compounds, converted from the above substituent-eliminable derivatives, have a solubility of 0.05% by weight or less in all the solvents. This means that soluble groups which constitute the substituent-eliminable derivatives make a significant contribution to the solubility. In other words, the elimination reaction converts the substituent-eliminable derivatives to the specific compounds that are more insoluble in the solvents.

Example 8

Evaluation of Wavelength Shift by Absorption Spectrum

Figure 5:
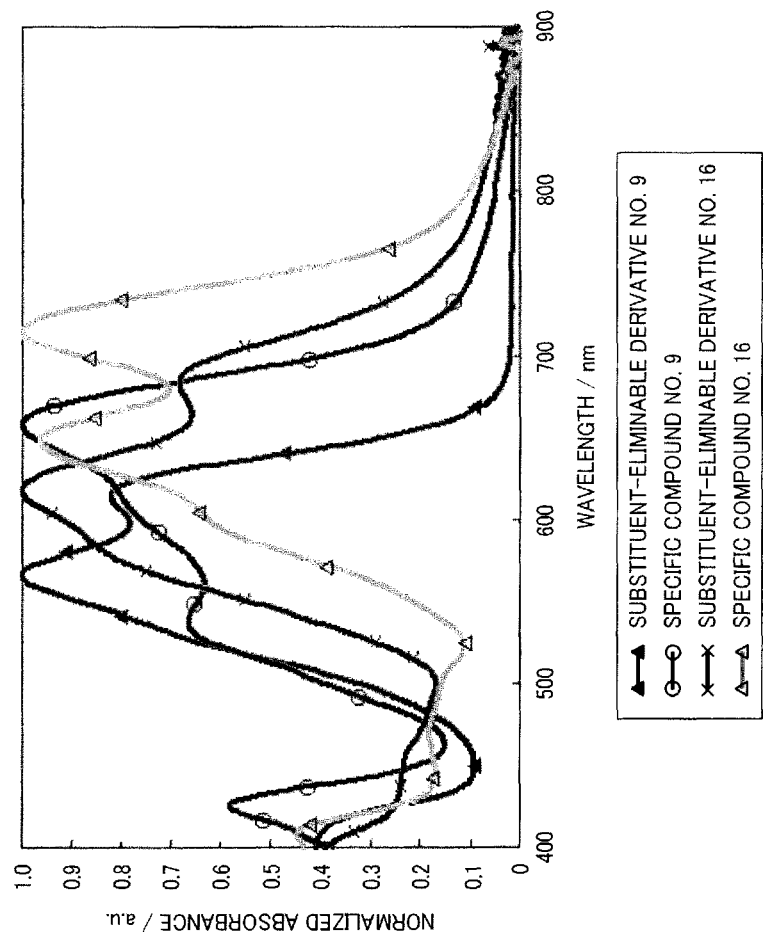
FIG. 5 is a graph showing the evaluation result of wavelength shift of absorption spectrum in Example 8.

Dissolve each of the substituent-eliminable derivatives obtained in Examples 2 and 3 in chloroform (2.0 mg/1 ml). Form a thin film of the solution on a glass substrate by spin coater and measure its absorption spectrum by an instrument V-660DS from JASCO Corporation. Heat the substrate to 220° C. for 5 minutes to eliminate the eliminable group and then measure the absorption spectrum with the instrument. The results are shown in FIG. 5.

Comparative Example 1

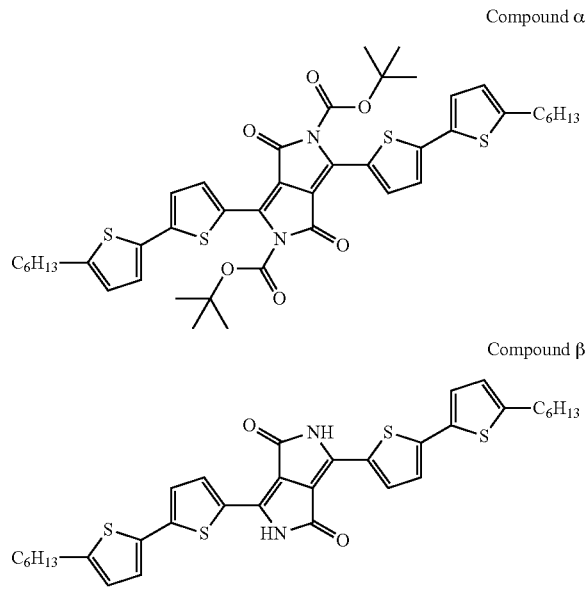

(Compound β is a conversion product of Compound α being heated at 220° C. for 5 minutes.)

Figure 6:
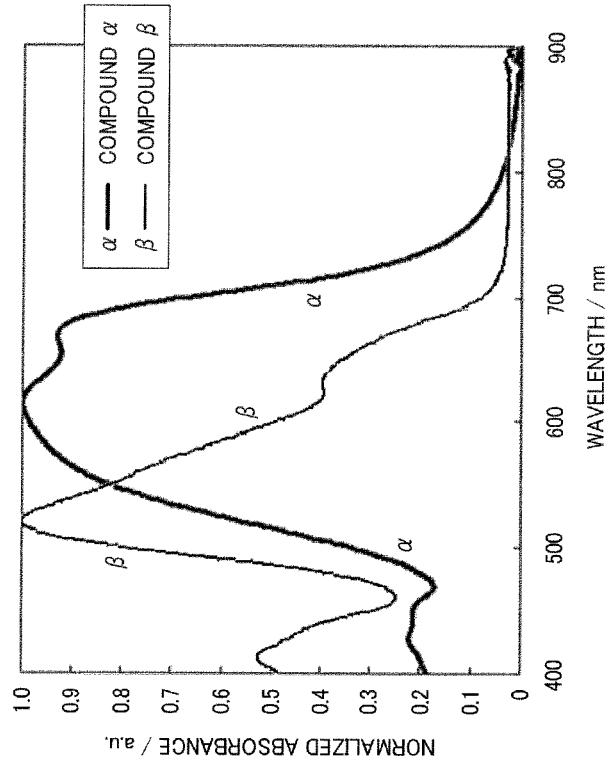
FIG. 6 is a graph showing the evaluation result of wavelength shift of absorption spectrum in Comparative Example 1.

Measure absorption spectra of the Compounds α and β in the same manner as in Example 8. The results are shown in FIG. 6.

The results of Example 8 and Comparative Example 1 indicate that the substituent-eliminable derivative according to an embodiment of the invention does not shift its absorption spectrum toward shorter wavelengths and rather shifts it toward longer wavelengths through the elimination of the substituent. By contrast, the substituent-eliminable derivative of Comparative Example 1 shifts its absorption spectrum toward shorter wavelengths through the elimination of the substituent. Never shifting the absorption spectrum toward shorter wavelengths, the substituent-eliminable derivative according to an embodiment of the invention is advantageous in energy matching with solar light when it is applied to optical organic devices such as organic thin film solar cells.

The substituent-eliminable derivative according to an embodiment of the present invention has good solubility in various organic solvents and is convertible into a specific compound (an organic semiconductor compound, etc.) at a high yield through the elimination reaction, providing excellent processability.

Even poorly-soluble organic semiconductor compounds which are generally difficult to be formed into a film can be easily formed into a continuous organic semiconductor film with use of the substituent-eliminable derivative according to an embodiment of the invention. Specifically, by forming the substituent-eliminable derivative according to an embodiment of the invention, employed as a precursor of such an organic semiconductor compound, into a film and then converting it into the objective organic semiconductor compound by application of heat, etc., a continuous organic semiconductor film can be obtained. Never shifting the absorption spectrum toward shorter wavelengths, the substituent-eliminable derivative according to an embodiment of the invention is advantageous in energy matching with solar light when it is applied to optical organic devices such as organic solar cells, leading to high efficiency. The organic semiconductor films thus formed can be applied to organic electronic devices. In particular, they are expected to be applied to the fields of electronic devices such as semiconductors, optical electronic devices such as EL light-emitting elements, electronic papers, sensors, and RFIDs (radio frequency identification).

What is claimed is:

1. A substituent-eliminable diketopyrrolopyrrole derivative represented by the following formula (I):

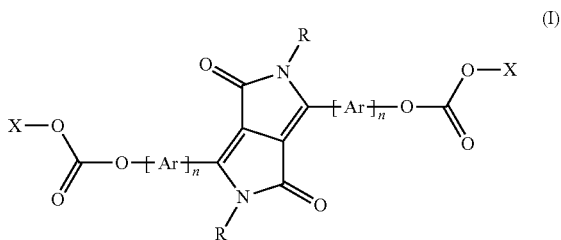

wherein R represents a substituted or unsubstituted alkyl group; X represents a substituted or unsubstituted alkyl group; Ar represents a substituted or unsubstituted aromatic group or a substituted or unsubstituted heteroaromatic group; and n represents an integer of from 1 to 4.

2. The substituent-eliminable diketopyrrolopyrrole derivative according to claim 1, wherein n is 2 or 3.

3. An organic semiconductor material precursor solution, comprising:
   the substituent-eliminable diketopyrrolopyrrole derivative according to claim 1; and
   a solvent.

* * * * *